(12) United States Patent
Cai et al.

(10) Patent No.: US 11,781,985 B2
(45) Date of Patent: *Oct. 10, 2023

(54) LIGHT DETECTION DEVICES WITH PROTECTIVE LINER AND METHODS RELATED TO SAME

(71) Applicant: Illumina, Inc., San Diego, CA (US)

(72) Inventors: Xiuyu Cai, San Diego, CA (US); Joseph Francis Pinto, Solana Beach, CA (US); Thomas A. Baker, San Diego, CA (US); Tracy Helen Fung, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/145,105

(22) Filed: Dec. 22, 2022

(65) Prior Publication Data

US 2023/0125640 A1    Apr. 27, 2023

Related U.S. Application Data

(63) Continuation of application No. 17/190,094, filed on Mar. 2, 2021, now Pat. No. 11,543,352, which is a
(Continued)

(30) Foreign Application Priority Data

Mar. 19, 2018    (NL) ..................... 2020612

(51) Int. Cl.
*G01N 21/64*    (2006.01)
*B01L 3/00*    (2006.01)
(Continued)

(52) U.S. Cl.
CPC ........ *G01N 21/6428* (2013.01); *B01L 3/5085* (2013.01); *B01L 3/50853* (2013.01);
(Continued)

(58) Field of Classification Search
CPC .......... G01N 21/6428; G01N 21/6454; G01N 33/582; G01N 21/05; G01N 2021/6439;
(Continued)

(56) References Cited

U.S. PATENT DOCUMENTS 5,846,708 A    12/1998 Hollis et al.
6,030,883 A    2/2000 Nishimoto et al.
(Continued)

FOREIGN PATENT DOCUMENTS

CN    101281887 A    10/2008
CN    102706954 A    10/2012
(Continued)

*Primary Examiner* — Jennifer Wecker
*Assistant Examiner* — Jonathan Bortoli
(74) *Attorney, Agent, or Firm* — HESLIN ROTHENBERG FARLEY & MESITI PC; Kristian E. Ziegler, Esq.

(57) ABSTRACT

Light detection devices and related methods are provided. The devices may comprise a reaction structure for containing a reaction solution with a relatively high or low pH and a plurality of reaction sites that generate light emissions. The devices may comprise a device base comprising a plurality of light sensors, device circuitry coupled to the light sensors, and a plurality of light guides that block excitation light but permit the light emissions to pass to a light sensor. The device base may also include a shield layer extending about each light guide between each light guide and the device circuitry, and a protection layer that is chemically inert with respect to the reaction solution extending about each light guide between each light guide and the shield layer. The protection layer prevents reaction solution that passes through the reaction structure and the light guide from interacting with the device circuitry.

20 Claims, 13 Drawing Sheets

Related U.S. Application Data continuation of application No. 16/216,014, filed on Dec. 11, 2018, now Pat. No. 10,955,343.

(60) Provisional application No. 62/609,889, filed on Dec. 22, 2017.

(51) Int. Cl.

| | | |
|---|---|---|
| *G01J 1/44* | (2006.01) | |
| *G01N 33/58* | (2006.01) | |
| *G02B 6/42* | (2006.01) | |
| *H01L 27/144* | (2006.01) | |
| *H01L 27/146* | (2006.01) | |
| *H01L 31/02* | (2006.01) | |
| *H01L 31/0216* | (2014.01) | |
| *H01L 31/0232* | (2014.01) | |
| *G01N 21/05* | (2006.01) | |

(52) U.S. Cl.
CPC .......... *B01L 3/502715* (2013.01); *G01J 1/44* (2013.01); *G01N 21/6454* (2013.01); *G01N 33/582* (2013.01); *G02B 6/4214* (2013.01); *H01L 27/1446* (2013.01); *H01L 27/14609* (2013.01); *H01L 27/14623* (2013.01); *H01L 27/14629* (2013.01); *H01L 31/02019* (2013.01); *H01L 31/02164* (2013.01); *H01L 31/02165* (2013.01); *H01L 31/02327* (2013.01); *G01N 21/05* (2013.01); *G01N 2021/6439* (2013.01)

(58) Field of Classification Search
CPC ............ B01L 3/502715; B01L 3/5085; B01L 3/50853; G01J 1/44; G01J 3/4406; G01J 3/0218; G02B 6/4214; H01L 27/1446; H01L 27/14609; H01L 27/14623; H01L 27/14629; H01L 31/02019; H01L 31/02164; H01L 31/02165; H01L 31/02327

See application file for complete search history.

(56) References Cited

U.S. PATENT DOCUMENTS

| | | |
|---|---|---|
| 8,906,320 B1 | 12/2014 | Eltoukhy et al. |
| 9,373,732 B2 | 6/2016 | Velichko et al. |
| 9,704,898 B2 | 7/2017 | Chung et al. |
| 9,842,870 B2 | 12/2017 | Chung et al. |
| 2005/0244870 A1 | 11/2005 | Chee et al. |
| 2008/0132072 A1* | 6/2008 | Letz ................ H01L 23/296 438/694 |
| 2008/0138006 A1 | 6/2008 | Lu et al. |
| 2015/0050187 A1 | 2/2015 | Mogi et al. |
| 2015/0056097 A1 | 2/2015 | Vaartstra |
| 2015/0079596 A1 | 3/2015 | Eltoukhy et al. |
| 2015/0243805 A1 | 8/2015 | Chien |
| 2016/0356715 A1* | 12/2016 | Zhong ............... G01N 21/6454 |
| 2017/0016830 A1 | 1/2017 | Chung et al. |
| 2017/0271388 A1 | 9/2017 | Chung et al. |
| 2018/0101100 A1 | 4/2018 | Tsubaki et al. |
| 2021/0208072 A1 | 7/2021 | Cai et al. |

FOREIGN PATENT DOCUMENTS

| | | |
|---|---|---|
| CN | 104048919 A | 9/2014 |
| CN | 105448863 A | 3/2016 |
| CN | 105980832 A | 9/2016 |
| CN | 106353285 A | 1/2017 |
| EP | 0808808 | 11/1997 |
| EP | 2221606 | 8/2010 |
| JP | 1036145 | 2/1998 |
| JP | 2002000903 | 1/2002 |
| JP | 2002296175 | 10/2002 |
| JP | 2003505109 | 2/2003 |
| JP | 2008522408 | 6/2008 |
| JP | 2010225939 | 10/2010 |
| JP | 2012000811 | 1/2012 |
| JP | 2017504789 | 2/2017 |
| KR | 1020160096644 | 8/2016 |
| TW | 201704903 A | 2/2017 |
| WO | 2000034457 | 6/2000 |
| WO | 2000036445 | 6/2000 |
| WO | 2004069983 | 8/2004 |
| WO | 2016030710 | 3/2016 |
| WO | 2016208299 | 12/2016 |

\* cited by examiner

LIGHT DETECTION DEVICES WITH PROTECTIVE LINER AND METHODS RELATED TO SAME

CROSS-REFERENCE TO RELATED APPLICATIONS

This present application is a continuation of U.S. patent application Ser. No. 17/190,094, filed Mar. 2, 2021, and entitled Light Detection Devices With Protective Liner and Methods Related to Same, which is a continuation of U.S. patent application Ser. No. 16/216,014, filed Dec. 11, 2018, and entitled Light Detection Devices With Protective Liner and Methods Related to Same, which claims priority to U.S. Provisional Patent Application No. 62/609,889, filed Dec. 22, 2017, and entitled Light Detection Devices with Protective Liner and Methods of Manufacturing Same, and Dutch Application No. 2020612, filed on Mar. 19, 2018, and entitled Light Detection Devices with Protective Liner and Methods of Manufacturing Same. The entire contents of each of the aforementioned applications are hereby incorporated herein by reference.

BACKGROUND

Various protocols in biological or chemical research involve performing a large number of controlled reactions on local support surfaces or within predefined reaction chambers. The designated reactions may then be observed or detected and subsequent analysis may help identify or reveal properties of substances involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may be emitted from the analytes. However, such optical systems can be relatively expensive and involve a relatively large benchtop footprint. For example, such optical systems may include an arrangement of lenses, filters, and light sources.

In other proposed detection systems, the controlled reactions occur on local support surfaces or within predefined reaction chambers provided over an electronic solid-state light detector or imager (e.g., a complementary metal-oxide-semiconductor (CMOS) detector or a charged-coupled device (CCD) detector) that does not involve a large optical assembly to detect the fluorescent emissions. However, such proposed solid-state imaging systems may have some limitations. For example, fluidically delivering reagents (e.g., fluorescently-labeled molecules) in a solution to the analytes that are located on the electronic device of such systems may present challenges. In some scenarios, the reagent solution may breach the electronic device and corrode or otherwise deteriorate components thereof, for example.

BRIEF DESCRIPTION

In one aspect of the present disclosure, a device is provided. The device comprises a reaction structure that forms a plurality of reaction recesses for containing a reaction solution with a pH of less than or equal to about 5 or a pH greater than or equal to about 8 and at least one reaction site that generates light emissions in response to incident excitation light after treatment with the reaction solution. The device also comprises a device base positioned beneath the reaction structure. The device base comprises a plurality of light sensors, and device circuitry electrically coupled to the light sensors to transmit data signals based on photons detected by the light sensors. The device base also comprises a plurality of light guides with input regions that receive the excitation light and the light emissions from at least one corresponding reaction recess, the light guides extending into the device base from the input regions toward at least one corresponding light sensor and comprising at least one filter material that filters the excitation light and permits the light emissions to pass to the at least one corresponding light sensor. The device further comprises a shield layer extending about each light guide and positioned between each light guide and the device circuitry. The device base also comprises a protection layer extending about each light guide and positioned between each light guide and the shield layer that prevents reaction solution that passes through the reaction structure and the light guide from interacting with the device circuitry. The protection layer is chemically inert with respect to the reaction solution.

In some examples, the protection layer abuts the plurality of light guides within the device base. In some such examples, the device circuitry is provided within dielectric material layers of the device base, the shield layer is positioned between the protection layer and the dielectric material layers, and the shield layer abuts the dielectric material layers.

In some examples, the protection layer further extends between a top surface of the device base and interstitial areas of the reaction structure that extend about the reaction recesses. In some such examples, the shield layer extends between the protection layer and the top surface of the device base.

In some examples, the protection layer comprises silicon dioxide, a metal oxide, a metal nitride or a combination thereof. In some examples, the protection layer comprises silicon dioxide, silicon oxynitride, silicon monoxide, silicon carbide, silicon oxycarbide, silicon nitrocarbide, metal oxide, metal nitride or a combination thereof. In some such examples, the pH of the reaction solution is greater than or equal to about 8. In some examples, the pH of the reaction solution is less than or equal to about 5, and the protection layer comprises silicon carbide, silicon oxycarbide, silicon nitrocarbide, a metal oxide, a metal nitride or a combination thereof. In some examples, the protection layer comprises a liquid impervious barrier layer. In some examples, the shield layer comprises a silicon nitride shield layer.

In some examples, the device circuitry comprises interconnected conductive elements, and the protection layer prevents the reaction solution from oxidizing the conductive elements. In some examples, the thickness of the protection layer is within the range of about 5 nanometers to about 100 nanometers. In some examples, the reaction structure comprises at least one reaction site immobilized to the reaction structure within each of the plurality of reaction recesses, and the reaction solution may initiate a reaction and/or form a reaction product with the at the at least one reaction site that generates light emissions in response to the incident excitation light. In some such examples, the at least one reaction site comprises at least one analyte, and the reaction solution comprises at least one fluorescently-labeled molecule.

In some examples, the device circuitry of the device base forms complementary metal-oxide semiconductor (CMOS) circuits.

In another aspect of the present disclosure, a biosensor is provided. The biosensor comprises any one of the devices described above. The biosensor also comprises a flow cell mounted to the device. The flow cell comprises the reaction solution and at least one flow channel that is in fluid communication with the plurality of reaction recesses of the reaction structure to direct the reaction solution thereto.

In another aspect of the present disclosure, a method is provided. The method comprises forming a plurality of trenches within a device base comprising a plurality of light sensors and device circuitry electrically coupled to the light sensors to transmit data signals based on photons detected by the light sensors, the plurality of trenches extending from a top surface of the device base and toward at least one corresponding light sensor. The method also comprises depositing a shield layer over the device base such that the shield layer extends at least within the plurality of trenches, and depositing a protection layer over the shield layer such that the protection layer extends at least within the plurality of trenches. The method further comprises filling the plurality of trenches over the deposited protection layer with at least one filter material to form a plurality of light guides, the at least one filter material filters light of at least a first wavelength and permits light of a second wavelength to pass therethrough to the at least one corresponding light sensor. The method also comprises forming a reaction structure over the plurality of light guides and the protection layer, the reaction structure forming a plurality of reaction recesses corresponding to at least one light guide for containing a reaction solution with a pH of less than or equal to about 5 or a pH greater than or equal to about 8 and at least one reaction site that generates light emissions of the second wavelength in response to incident excitation light of the first wavelength after treatment with the reaction solution. The protection layer is chemically inert with respect to the reaction solution.

In some examples, the protection layer comprises silicon dioxide, silicon oxynitride, silicon monoxide, silicon carbide, silicon oxycarbide, silicon nitrocarbide, silicon dioxide, metal oxide, metal nitride or a combination thereof, and wherein the shield layer comprises a silicon nitride shield layer. In some examples, depositing the shield layer over the device base further comprises depositing the shield layer over the top surface of the device base, and depositing the protection layer over the device base further comprises depositing the protection layer over the portion of the shield layer extending over the top surface of the device base.

In some examples, the method further comprises passing the reaction solution with a pH of less than or equal to about 5 or a pH greater than or equal to about 8 over the reaction structure.

It should be appreciated that all combinations of the foregoing aspects and additional concepts discussed in greater detail below (provided such concepts are not mutually inconsistent) are contemplated as being part of the inventive subject matter disclosed herein.

These and other objects, features and advantages of this disclosure will become apparent from the following detailed description of the various aspects of the disclosure taken in conjunction with the accompanying drawings.

DRAWINGS

These and other features, aspects, and advantages of the present disclosure will become better understood when the following detailed description is read with reference to the accompanying drawings, which are not necessarily drawn to scale and in which like reference numerals represent like aspects throughout the drawings, wherein.

DETAILED DESCRIPTION

Figure 1:
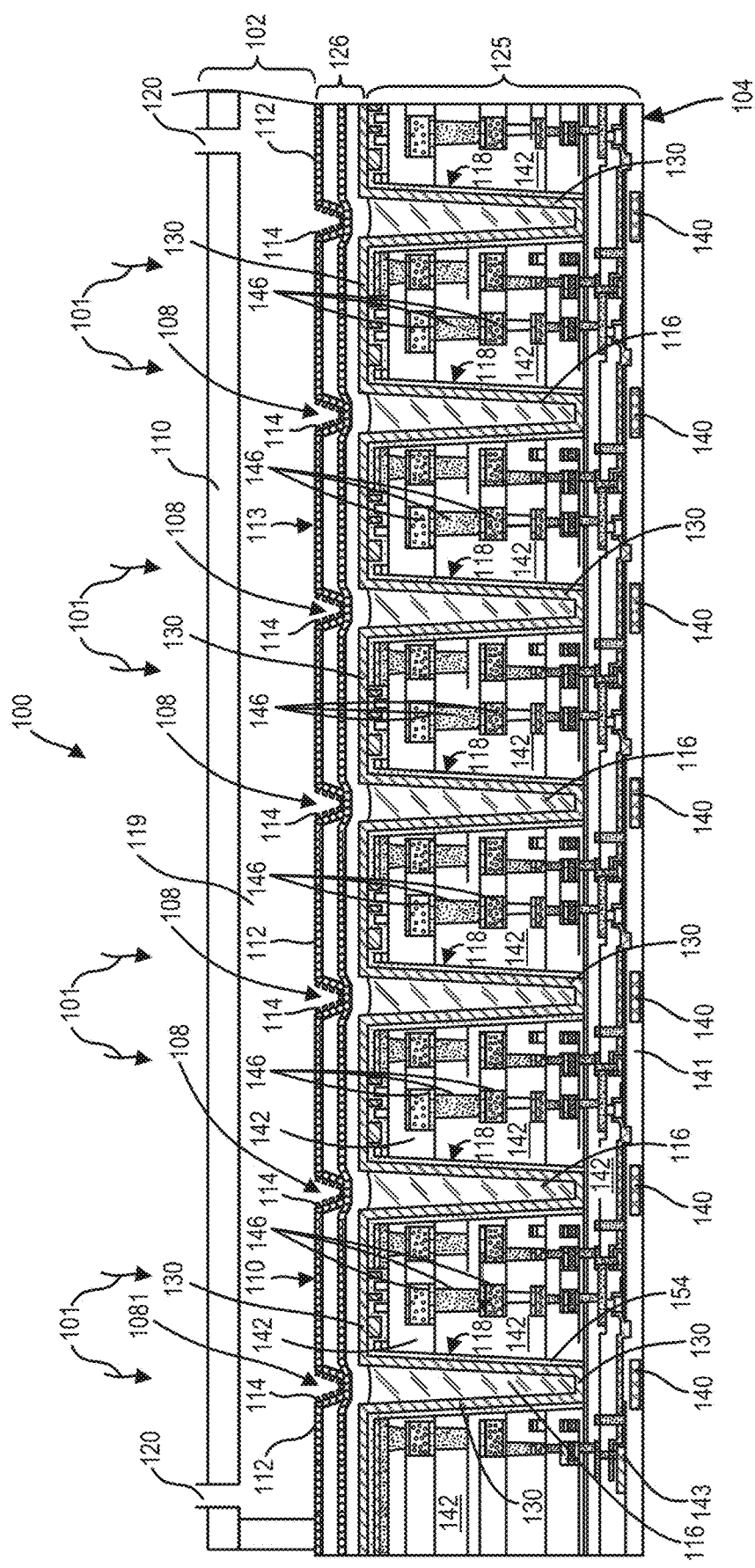
FIG. 1 illustrates, in one example, a cross-section of a biosensor in accordance with the present disclosure.

Aspects of the present disclosure and certain examples, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to an "example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel). A reaction recess may be at least partially separated from the surrounding environment other or spatial regions. For example, a plurality of reaction recesses may be separated from each other by shared walls, such as a detector surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

FIGS. 1-8 illustrate a cross-section of a portion of a biosensor 100 formed in accordance with one example. As shown, the biosensor 100 may include a flow cell 102 that is coupled directly or indirectly to a light detection device 104. The flow cell 102 may be mounted to the light detection device 104. In the illustrated example, the flow cell 102 is affixed directly to the light detection device 104 through one or more securing mechanisms (e.g., adhesive, bond, fasteners, and the like). In some examples, the flow cell 102 may be removably coupled to the light detection device 104.

The biosensor 100 and/or detection device 104 may be configured for biological or chemical analysis to obtain any information or data that relates thereto. In particular examples, the biosensor 100 and/or detection device 104 may comprise a nucleic acid sequencing system (or sequencer) configured for various applications, including but not limited to de novo sequencing, resequencing of whole genomes or target genomic regions, and metagenomics. The sequencing system may be configured to perform DNA or RNA analysis. In some examples, the biosensor 100 and/or detection device 104 is configured to perform a large number of parallel reactions within the biosensor 100 and/or detection device 104 to obtain information relating thereto.

The flow cell 102 may include one or more flow channels that direct a solution to or toward reaction sites 114 on the detection device 104, as explained further below. The flow cell 102 and/or biosensor 100 may thereby include, or be in fluid communication with, a fluid/solution storage system (not shown) that may store various reaction components or reactants that are used to conduct the designated reactions therein, for example. The fluid storage system may also store fluids or solutions for washing or cleaning a fluid network and the biosensor 100 and/or detection device 104, and potentially for diluting the reactants. For example, the fluid storage system may include various reservoirs to store samples, reagents, enzymes, other biomolecules, buffer solutions, aqueous, oil and other non-polar solutions, and the like. As noted above, the fluid or solution provided on the reaction structure 126 may be relatively acidic (e.g., pH less than or equal to about 5) or basic/alkaline (e.g., pH greater than or equal to about 8). Furthermore, the fluid storage system may also include waste reservoirs for receiving waste products from the biosensor 100 and/or detection device 104.

Figure 3:
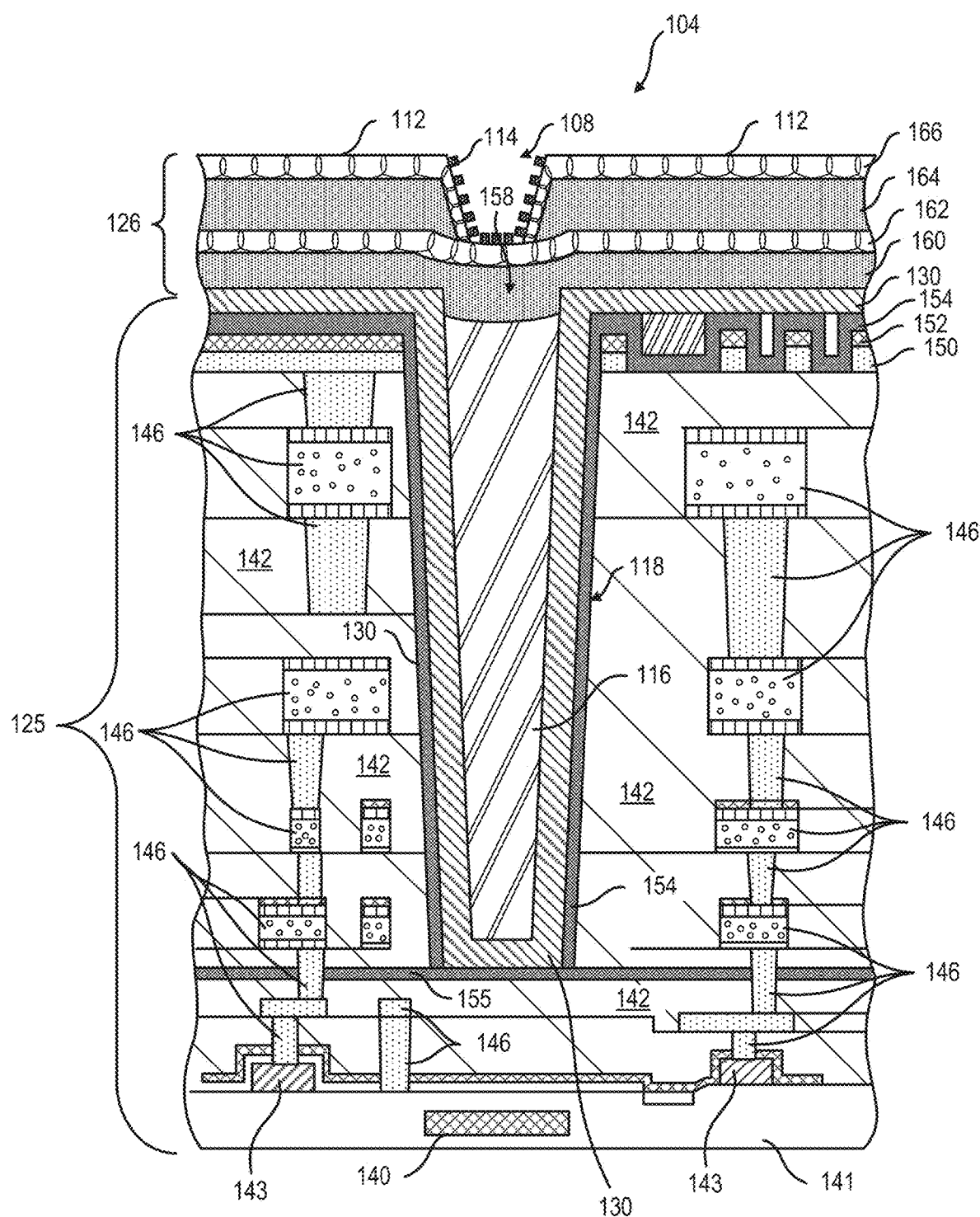
FIG. 3 illustrates, in one example, a cross-section of a portion of the detection device of FIG. 2 illustrating a portion of a reaction structure and a light guide thereof.

In the illustrated example, the light detection device 104 includes a device base 125 and a reaction structure 126 overlying the device base 125, as shown in FIGS. 1 and 3-8. In particular examples, the device base 125 includes a plurality of stacked layers (e.g., silicon layer or wafer, dielectric layer, metal-dielectric layers, etc.). The device base 125 may include a sensor array 124 of light sensors 140, and a guide array of light guides 118, as shown in FIG. 3. As shown in FIGS. 1 and 3-8, the reaction structure 126 may include an array of reaction recesses 108 that have at least one corresponding reaction site 114 provided therein (e.g., immobilized on a surface thereof). In certain examples, the light detection device 104 is configured such that each light sensor 140 corresponds (and potentially aligns) with a single light guide 118 and/or a single reaction recess 108 such that it receives photons only therefrom. However, in other examples, a single light sensor 140 may receive photons through more than one light guide 118 and/or from more than one reaction recess 108. A single light sensor 140 may thereby form one pixel or more than one pixel.

Figure 2:
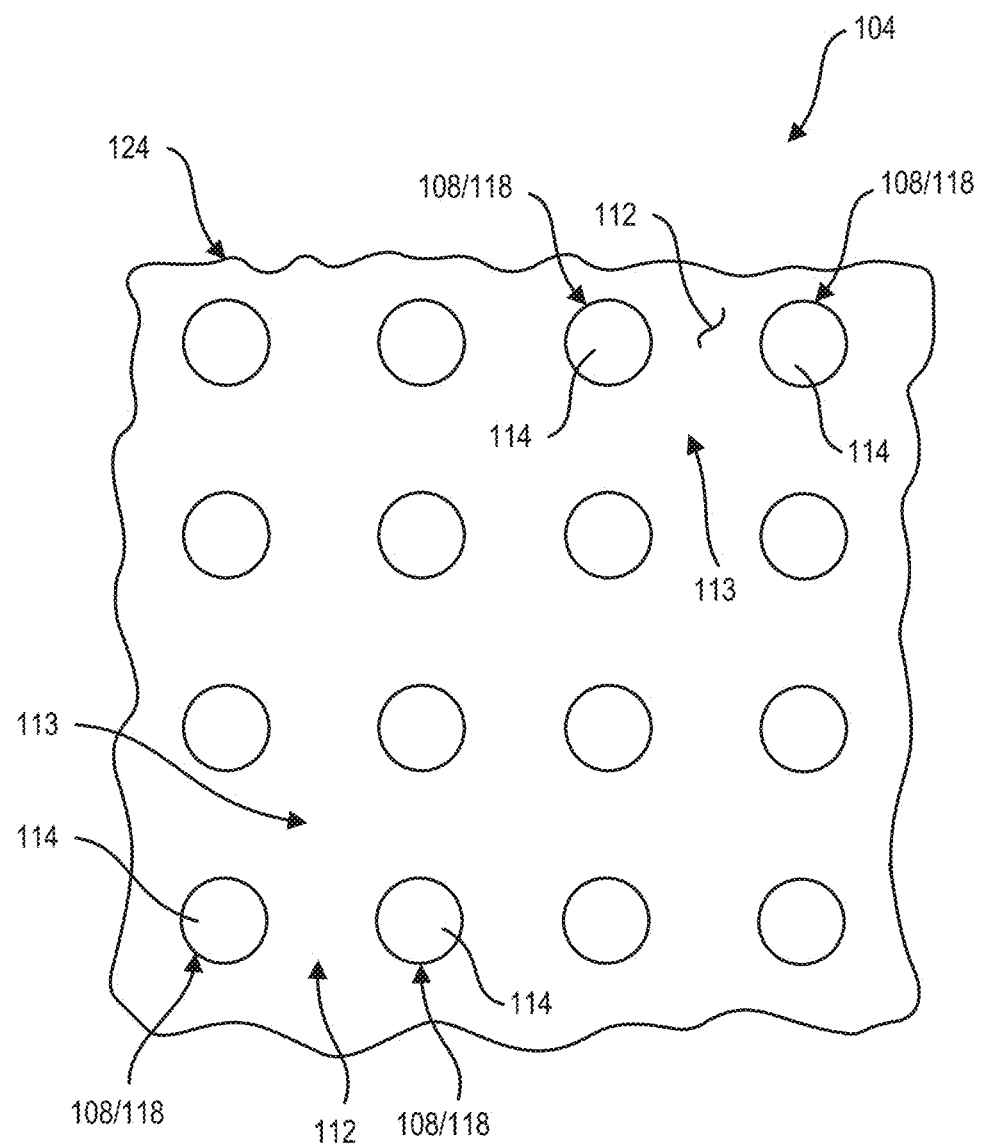
FIG. 2 illustrates, in one example, a top view of a detection device of the biosensor of FIG. 1.

As shown in FIG. 2, the array of reaction recesses 108 and/or light guides 118 (and potentially light sensors 140) may be provided in a defined repeating pattern such that at least some of the recesses 108 and/or light guides 118 (and potentially light sensors 140) are equally spaced from one another in a defined positional pattern. In other examples, the reaction recesses 108 and/or light guides 118 (and potentially light sensors 140) may be provided in a random pattern, and/or at least some of the reaction recesses 108 and/or light guides 118 (and potentially light sensors 140) may be variably spaced from each other.

As shown in FIGS. 1 and 2, the reaction structure 126 of the detection device 104 may define a detector surface 112 over which a reaction solution may flow and reside, as explained further below. The detector surface 112 of the reaction structure 126 may be the top exposed surface of the detection device 104. The detector surface 112 may comprise the surfaces of the recesses 108 and interstitial areas 113 extending between and about the recesses 108. As explained further below, the device base 125 of the detection device 104 may include a protection layer 130 that forms a smooth flat (e.g., planar) surface that underlying the support structure that minimizes surface topography modulation induced in the detector surface 112, and in particular to the interstitial areas 113 of the detector surface 112. In particular examples, the interstitial areas 113 of the detector surface 112 may be smooth planar surface portions that prevent the reaction solution and/or any other biological or chemical substances from remaining thereon and/or prevents pad hopping errors. The smoothness and/or flatness of the interstitial areas 113 of the detector surface 112 provided by the configuration of the underlying protection layer 130 may be smoother and/or flatter than as compared to examples that are void of the protection layer 130. Further, in some examples, the smoothness and/or flatness of the interstitial areas 113 of the detector surface 112 provided by the underlying protection layer 130 may enhance the robustness of the detection device 104 as compared to examples that are void of the protection layer 130.

Figure 4:
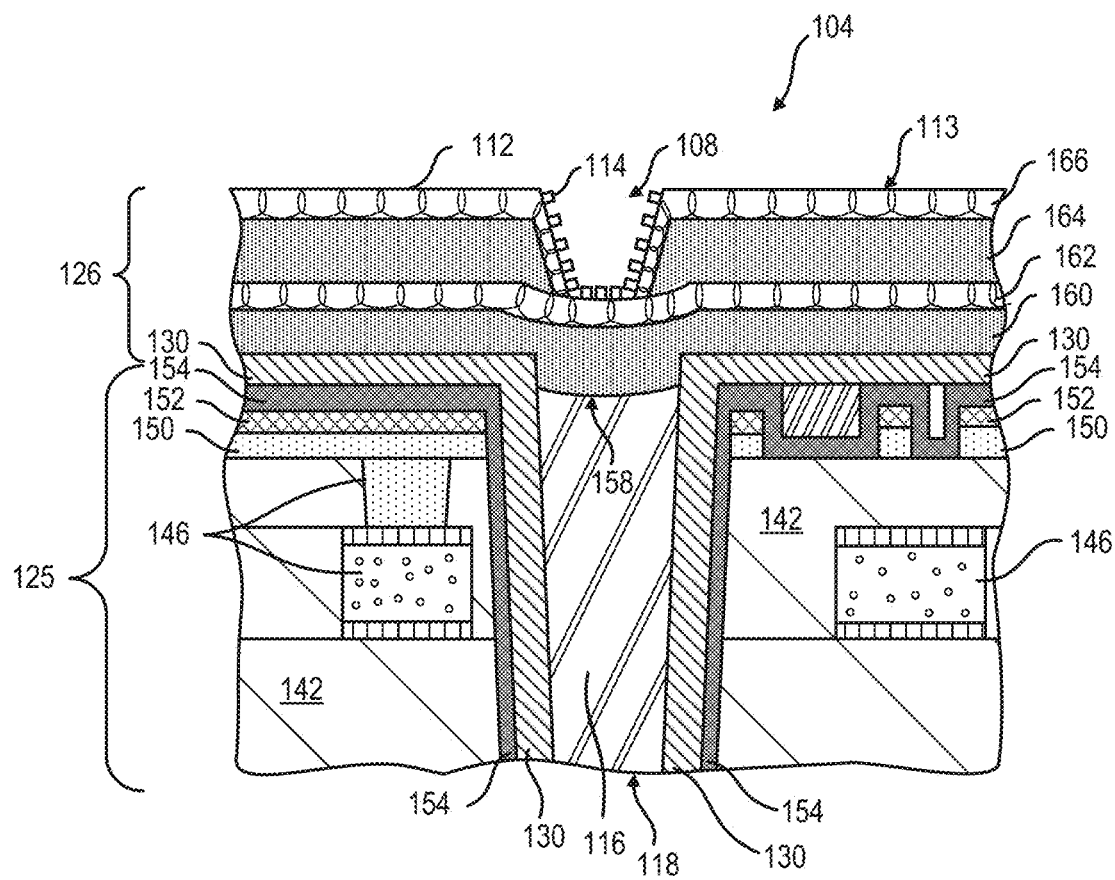
FIG. 4 illustrates, in one example, an enlarged portion of the cross-section of FIG. 3.

The detector surface 112 of the light detection device 104 may be functionalized (e.g., chemically or physically modified in a suitable manner for conducting designated reactions). For example, the detector surface 112 may be functionalized and may include a plurality of reaction sites 114 having one or more biomolecules immobilized thereto, as shown in FIGS. 1, 3 and 4. As noted above, the detector surface 112 may include an array of reaction recesses 108 (e.g., open-sided reaction chambers). Each of the reaction recesses 108 may include one or more of the reaction site 114. The reaction recesses 108 may be defined by, for example, a change in depth (or thickness) along the detector surface 112. In other examples, the detector surface 112 may be substantially planar.

As shown in FIGS. 3 and 4, the reaction sites 114 may be distributed in a pattern along the detector surface 112, such as within the reaction recesses 108. For instance, the reactions sites 114 may be located in rows and columns along the reaction recesses 108 in a manner that is similar to a microarray. However, it is understood that various patterns of reaction sites 114 may be used. The reaction sites 114 may include biological or chemical substances that emit light signals, as explained further below. For example, the biological or chemical substances of the reactions sites 114 may generate light emissions in response to the excitation light 101. In particular examples, the reaction sites 114 include clusters or colonies of biomolecules (e.g., oligonucleotides) that are immobilized on the detector surface 112 within the reaction recesses 108. The reactions sites 114 may generate light emissions in response to incident excitation light after treatment with the reaction solution. For example, the reaction solution may initiate a reaction and/or form a reaction product at the reactions sites 114 (but potentially not at other reaction sites of the reaction structure 126 of the device 104) that generates light emissions in response to the excitation light.

As shown in FIG. 1, in one example the flow cell 102 includes at least one sidewall and a flow cover 110. The at least one sidewall may be coupled to the detector surface 112 and extend between the flow cover 110 and the detector surface 112. The flow cell 102 may be configured so that a flow channel 119 is formed between the flow cover 110 and the detector surface 112 of the light detection device 104. In some examples, the flow channel 119 may include a height (extending between the flow cover 110 and the detector surface 112) within the range of about 50 to about 400 μm (microns), or more particularly about 80 to about 200 μm, for example. In one example, the height of the flow channel 119 is about 100 μm. The flow cover 110 may comprise a material that is transparent to the excitation light 101 propagating from an exterior of the biosensor 100 and toward/into the flow channel 119, as shown in FIG. 1. It is noted that excitation light 101 may approach the flow cover 110 from any angle, and along the same or different angles.

The excitation light 101 may be emitted from any illumination source (not shown), which may or may not be part of the bioassay system, biosensor 100 or light detection device 104. In some examples, the illumination system may include a light source (e.g., one or more LED), and, potentially, a plurality of optical components to illuminate at least the reaction structure 126 of the detection device 104. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In a particular example, the illumination system is configured to direct the excitation light 101 to reaction sites 114 within the recesses 108 of the reaction structure 126 of the detection device 104. In some examples, the illumination system may emit the excitation light 101 within a range of wavelengths, such as within the range of about 300 nm to about 700 nm for example, or more particularly within the range of about 400 nm to about 600 nm for example. In some examples, the illumination system may emit the excitation light 101 at a certain wavelength or wavelengths that excites the biological or chemical substance(s) of the reaction sites 108 (e.g., a reaction initiated by the reaction solution and/or reaction product form by the reaction solution at the reactions sites 114) to emit light emissions of a differing wavelength or wavelengths. For example, in one example where the reaction sites 108 include fluorophores excited by green wavelengths of light, the excitation light may be about 532 nm and the light emissions may be about 570 nm or more.

As also shown in FIG. 1, the flow cover 110 may include at least one port 120 that is configured to fluidically engage the flow channel 119 and, potentially, other ports (not shown). For example, the other ports may be from a cartridge or a workstation that comprised the reaction solution or another biological or chemical substance. The flow channel 119 may be configured (e.g., sized and shaped) to direct a fluid or solution, such as the reaction solution, along the detector surface 112.

FIGS. 3 and 4 show the detection device 104 in greater detail than FIG. 1. More specifically, FIGS. 3 and 4 show a single light sensor 140, a single light guide 118 for directing and passing light emissions from at least one reaction site 114 associated therewith toward the light sensor 140, and associated circuitry 146 for transmitting signals based on the light emissions (e.g., photons) detected by the light sensor 140. It is understood that the other light sensors 140 of the sensor array 124 (FIGS. 1 and 2) and associated components may be configured in an identical or similar manner. It is also understood, however, the light detection device 104 is not required to be manufactured uniformly throughout. Instead, one or more light sensors 140 and/or associated components may be manufactured differently or have different relationships with respect to one another.

The circuitry 146 may include interconnected conductive elements (e.g., conductors, traces, vias, interconnects, etc.) that are capable of conducting electrical current, such as the transmission of data signals that are based on detected photons. For example, in some examples, the circuitry 146 may comprise a microcircuit arrangement. The light detection device 104 and/or the device base 125 may comprise at least one integrated circuit having an array of the light sensors 140. The circuitry 146 positioned within the detection device 104 may be configured for at least one of signal amplification, digitization, storage, and processing. The circuitry 146 may collect (and potentially analyze) the detected light emissions and generate data signals for communicating detection data to a bioassay system. The circuitry 146 may also perform additional analog and/or digital signal processing in the light detection device 104.

The device base 125 and the circuitry 146 may be manufactured using integrated circuit manufacturing processes, such as processes used to manufacture charged-coupled devices or circuits (CCD) or complementary-metal-oxide semiconductor (CMOS) devices or circuits. For example, as shown in FIG. 3, the device base 125 may be a CMOS device comprising of a plurality of stacked layers including a sensor base 141, which may be a silicon layer (e.g., a wafer) in some examples. The sensor base 141 may include the light sensor 140, and gates 143 formed thereon. The gates 143 may be electrically coupled to the light sensor 140. When the light detection device 104 is configured as shown in FIG. 3, the light sensor 140 may be electrically coupled to the circuitry 146 through the gates 143, for example.

At least some of the circuitry 146 may be provided within device substrate layers of the device base 125 of the detection device 104, through/into which the lights guides 118 may each extend. In some examples, each of the substrate layers may include interconnected conductive elements that forms at least part of the device circuitry 146, and dielectric material 142 adjacent to (and potentially surrounding) the conductive elements of the circuitry 146, as shown in FIG. 3. The conductive elements of the circuitry 146 may be embedded within the dielectric material 142. As also shown in FIG. 3, the lights guides 118 may extend through the dielectric material 142 and may be spaced from the circuitry 146. Various metallic elements and/or dielectric materials may be used, such as those suitable for integrated circuit manufacturing (CMOS manufacturing). For example, in some examples, the conductive elements/circuitry 146 may be metallic elements, such as W (tungsten) elements, Cu (copper) elements, Al (aluminum) elements, or a combination thereof (but it is understood that other materials and configurations may be used). In some examples, the dielectric material may be SiO2 (but it is understood that other materials and configurations may be used).

As used herein, the term "layer" is not limited to a single continuous body of material unless otherwise noted. For example, the sensor base 141 and/or the device layers of the device base 125 may include multiple sub-layers that are different materials and/or may include coatings, adhesives, and the like. Furthermore, one or more of the layers (or sub-layers) may be modified (e.g., etched, deposited with material, etc.) to provide the features described herein.

As shown in FIGS. 3 and 4, the reaction structure 126 may comprise one or more layers that form the reaction recesses 104 extending therein. The reaction structure 126 may extend along a top outer surface of the device base 125. In the illustrated example, the reaction structure 126 is deposited directly along the top outer surface of a first shield layer 154 and the first and second filter material 116, 115 of the device base 125, as described further below. However, an intervening layer may be disposed between the reaction structure 126 and the device base 125 in other examples. The reaction structure 126 may include one or more materials that are configured to allow the excitation light signals 101 and emitted light signals from the reaction sites 114 (after treatment with the reaction solution) within the recesses 108 to pass therethrough and into an opening 158 of one or more light guide 118 corresponding to a particular reaction recess 108. In some examples, the reaction structure 126 may include one more layer or other feature that prevents crosstalk or "sharing" of emitted light from a particular reaction site 114/reaction recess 108 from passing to a non-corresponding sensor 140.

The reaction structure 126 may comprise a plurality of differing layers, as shown in FIGS. 3 and 4. In the illustrated example, the reaction structure 126 may include a first reaction layer 160 that extends over (directly or indirectly) device base 125 (e.g., over the first shield layer 154) and the opening 158 of the light guides 118 (e.g., the first and second filter material 116, 115) of the device base 125, as shown in FIGS. 3 and 4. As also shown in FIGS. 3 and 4, in the illustrated example, the reaction structure 126 further includes a second layer 162 that extends over (directly or indirectly) the first layer 160. The reaction structure 126 of illustrated example also includes a third layer 164 that extends over (directly or indirectly) the second layer 162, and a fourth layer 166 that extends over (directly or indirectly) the third layer 164. The reaction recesses 108 may extend at least into the third layer 164.

The fourth layer 166 may form the inner surfaces (e.g., side walls and a bottom wall) of the reaction recesses 108 by extending over an indentation (e.g., a cavity or a void) in the third layer 164, as shown in FIGS. 3 and 4. The fourth layer 166, and potentially the second layer 162, may form the detector surface 112, as shown in FIGS. 3 and 4. In some cases, the fourth layer 166, and potentially the second layer 162, may be configured to provide a solid surface that permits chemicals, biomolecules or other analytes-of-interest to be immobilized thereon. For example, each of the reaction sites 114 may include a cluster of biomolecules that are immobilized to the detector surface 112, which may comprise the fourth layer 166, and potentially the second layer 162. Thus, the fourth layer 166, and potentially the second layer 162, may comprise a material that permits the reaction sites 114 to be immobilized thereto. The first layer 160 and the fourth layer 166 (and potentially the second layer 162 and the third layer 166) may comprise a material that is at least substantially transparent to the excitation light 101 and the emission light of the reaction sites 114. In addition, the fourth layer 166, and potentially the second layer 162, may be physically or chemically modified to facilitate immobilizing the biomolecules and/or to facilitate detection of the light emissions.

By way of example and as shown in the illustrated example of FIGS. 3 and 4, the first layer 160 and the third layer 166 may comprise a first material, and the second layer 162 and the fourth layer 166 may comprise a second material that differs from the first material. In some such examples, the first material is SiN, and the second material is TaO. However, the reaction structure 126 may comprise differing layers (e.g., different layers, fewer layers, and/or additional layers) and/or differing materials.

As shown in FIGS. 3 and 4, the device base 125 of the detection device 104 may include a first shield layer 150 that extends over (directly or indirectly) the stacked layers (e.g., metal-dielectric layers) of the device base 125, such as over the dielectric material 142 and the conductive circuitry components 146. The first shield layer 150 may include a material that is configured to block, reflect, and/or significantly attenuate the excitation light 101 and/or the light emissions from the reaction sites 114 (e.g., light signals that are propagating from the flow channel 118). By way of example only, the first shield layer 150 may comprise tungsten (W).

The first shield layer 150 may include at least one an aperture therethrough which aligns, at least partially, with at least one corresponding light guide 118. The first shield layer 150 may include an array of such apertures. In some examples, the first shield layer 150 may extend entirely about the apertures therein. As such, the light signals from excitation light 101 and/or the light emissions from the reaction sites 114 may be blocked, reflected, and/or significantly attenuated to prevent the light signals from passing through the device base 125 outside of the light guides 118 and being detected by the light sensors 140. In some examples, the first shield layer 150 extends continuously between adjacent light guides 118 and/or openings extending thereto. In some other examples, the first shield layer 150 does not extend continuously between adjacent light guides 118 and/or openings extending thereto such that one or more other opening exists in the first shield layer 150, which may allow the excitation light 101 and/or the light emissions from the reaction sites 114 to pass therethrough.

In some examples, the device base 125 of the detection device 104 may include a second shield layer 152 that extends over (directly or indirectly) the first shield layer 150, as shown in FIGS. 3 and 4. The second shield layer 152 may include anti-reflective material and/or a material that prevents contamination of the underlying portions of the device base 125. By way of example only, the second shield layer 152 may comprise SiON. In some examples, the second shield layer 152 may be configured to prevent contaminated, such as sodium, from interacting with the first shield layer 150, the dielectric material 142 and/or the conductive (e.g., metal) components of the device circuitry 146. In some examples, the second shield layer 152 may mimic the configuration of the first shield layer 150. For example, the second shield layer 152 may include at least one aperture therethrough which aligns, at least partially, with at least one light guide 118, as shown in FIGS. 3 and 4. The second shield layer 152 may include an array of such apertures. In some examples, the second shield layer 152 may extend about the apertures therein. In some examples, the second shield layer 152 extends continuously between adjacent light guides 118 and/or openings extending thereto. In some other examples, the second shield layer 152 does not extend continuously between adjacent light guides 118 and/or openings extending thereto such that one or more other aperture exists in the second shield layer 152, as shown in FIGS. 3 and 4.

In some examples, the light detection device 104 may include a liner layer 154 that extends over the device base 125 and about the light guides 118, as shown in FIGS. 3 and 4. The liner layer 154 may be a continuous conformal layer formed on the device base 125. The liner layer 154 may be chemically reactive with respect to the reaction solution. For example, due to the composition (e.g., water and/or oil) and/or relatively high acidity (e.g., pH equal to or less than about 5) or relatively high basicity (e.g., pH equal to or greater than about 8) of the reaction solution, the reaction solution may chemically react with the material of the liner layer 154 when exposed thereto and cause the material to be dissolved or otherwise detached (i.e., etch the liner layer 154). Over exposure time, the reaction solution may thereby etch through the liner layer 154 and, ultimately, interact with and corrode or otherwise interfere with the functioning of the device circuitry 146. For example, the liner layer 154 may be a silicon nitride layer (or otherwise include SiN), and the relatively high acidic or basic reaction solution may tend to etch the SiN when exposed thereto. In this way, the SiN liner layer 154 may be ineffective in preventing the reaction solution from etching therethrough and, ultimately, interacting with the device circuitry 146 (e.g., corroding the conductive (e.g., metal) components of the device circuitry 146). Other materials forming the liner layer 154 may be similarly chemically reactive to the reaction solution, such as due to the composition and/or relatively high acidity or basicity thereof, and thereby fail to prevent the reaction solution from etching therethrough over time.

The liner layer 154 may be void of defined apertures. However, the liner layer 154 may include at least one internal discontinuity, pore, crack, break or the like that allows a liquid or solution, such as the reaction solution, to flow through the liner layer 154, as explained further below. For example, the density of the liner layer 154 may be relatively low such that internal discontinuities thereof form a pathway through the liner layer 154, through which the reaction solution may pass to the dielectric material 142 and, ultimately, the conductive (e.g., metal) components of the device circuitry 146. In this way, the liner layer 154 may be ineffective in preventing the reaction solution from passing therethrough and, ultimately, interacting with the device circuitry. In some example, due to its density or internal discontinuities, the liner layer 154 may not be liquid impervious.

In the illustrated examples, the liner layer 154 extends between the second shield layer 152 and the protection layer 130 on the top upper portion of the device base 125, and extends along the light guides 118 between the dielectric material layers 142 and the protection layer 130. The liner layer 154 may be configured as an anti-reflective or a reflective layer (e.g., to ensure the light emitted from the reaction sites 114 passes through the light guides 118), a contamination prevention layer (e.g., to prevent sodium contamination into the device base 125) and/or an adhesion layer (e.g., to adhere the filter material 116 of the light guides 118 to the dielectric material 142). In some examples, the liner layer 154 may be configured as a contamination prevention layer that prevents any ionic species from penetrating into device layers (e.g., metal-dielectric layers). In some examples, the liner layer 154 comprises SiN. In some examples, the liner layer 154 comprises a SiN layer.

As shown in FIGS. 3 and 4, the liner layer 154 may be of a substantially uniform thickness. In other examples, the thickness of the liner layer 154 may vary. For example, the portions of the liner layer 154 extending over the top portion of the device base 125 may be a first thickness, and the portions of the liner layer 154 extending about the light guides 118 may be a second thickness that is thicker or thinner than the first thickness. As another example, the thickness of the portions of the liner layer 154 extending about the light guides 118 may vary along the depth within the device base 125 (e.g., may taper with depth into the device base 125). In some examples, the thickness of the liner layer 154 may be within the range of about 10 nm to about 100 nm. In the illustrated example, the liner layer 154 is about 50 nm thick.

As shown in FIG. 3, the device base 125 may also include a second liner layer 155 formed within the device layers of the device base 125 and beneath the light guides 118. The second liner layer 155 may be substantially similar or the same as the liner layer 154 but for its position within the device base 125. In some examples, the second liner layer 155 may extend immediately below the protection layer 130 along the bottom of the light guides 118, as shown in FIG. 3. In this way, the liner layer 154 and the second liner layer 155 may extend entirely about the light guides 118 but for the openings 158 of the light guides 118 beneath the recesses 108. The second liner layer 155 may form the bottom of the light guides 118.

As discussed above, the device base 125 of the detection device 104 may include the protection liner layer 130 positioned between each light guide 118 and the device circuitry 146, as shown in FIGS. 3 and 4. The protection layer 130 may extend over (directly or indirectly) the liner layer 154 on top of the device base 125 and along the light guides 118, as shown in FIGS. 3 and 4. In some examples (not shown), the protection layer 130 may not extend over (directly or indirectly) the top of the device base 125 beneath the reaction structure 126, and may only extend along/about the light guides 118 within the device base 126 (i.e., only be positioned between the dielectric material 142 and the filter material 116).

The protection layer 130 may extend fully about the filter material 116 of the light guides 118 but for the openings 158 thereof. For example, the protection layer 130 may extend about the side surfaces of the light guides 118, and below the light guides 118 (between the liner layer 154 and the second liner layer 155 and the filter material 116). The protection layer 130 may also be provided on the device base 125 (e.g., directly over the liner layer 154) and the reaction structure 126. The protection layer 130 may also thereby be provided over the top portion of device base 125 and positioned between the device base 125 and the reaction structure 126.

The protection layer 130 may be a continuous coating layer. The protection layer 130 may be void of predefined or purposely-formed apertures or other voids that would allow a liquid or solution, such as the reaction solution, to flow therethrough. The protection layer 130 may also be void of any internal discontinuities, pores, cracks, breaks or the like, or prevent the formation thereof, that would allow a liquid or solution, such as the reaction solution, to flow therethrough, as explained further below. The protection layer 130 may thereby be a liquid impervious barrier. A liquid impervious layer herein refers to a layer that may prevent any liquid or solution (e.g., the reaction solution) from passing therethrough, such as preventing at least about 99 vol % of the reaction solution in contact with the protection layer 130 at about atmospheric pressure from passing therethrough. The protection layer 130 may also be chemically inert with respect to the reaction solution such that the reaction solution (which may include a relatively high acidity or relatively high basicity, as described above) does not etch the protection layer 130, or etches less than about one (1) angstrom (Å) of the thickness of the protection layer 130 per hour at about 100 degrees Celsius and at about atmospheric pressure, when the reaction solution is in contact with the protection layer 130. For example, the composition of the protection layer 130 may not chemically react, or chemically reacts to only a relatively small degree, with the composition of the reaction solution (which may include a relatively high acidity or relatively high basicity) such that the reaction solution does not etch the protection layer 130 or etches less than about one (1) angstrom (Å) of the thickness of the protection layer 130 per hour at about 100 degrees Celsius and at about atmospheric pressure when the reaction solution is in contact with the protection layer 130. The liner layer 154 may thereby comprise an etch resistant layer with respect to the reaction solution (which may include a pH equal to or less than about 5 or a pH equal to or greater than about 8, for example) to prevent the reaction solution from penetrating therethrough (over time) and, ultimately, interacting with and corroding or otherwise interfering with the functioning of the device circuitry 146. The protection layer 130 is thereby configured to prevent a liquid or solution (such as the reaction solution) that may penetrate through the reaction structure 126 to the protection layer 130, or through the reaction structure 126 and the filter material 116 of a light guide 118 to the protection layer 130, from interacting with the device circuitry 146 (and the liner layer 154 (if provided) and the dielectric material 142).

The thickness of the protection layer 130 may vary. For example, the portions of the protection layer 130 extending over the top portion of the device base 125 may be a first thickness, and the portions of the protection layer 130 extending about the light guides 118 and/or below the light guides 118 may be a second thickness that is thicker or thinner than the first thickness. As another example, the thickness of the portions of the protection layer 130 extending about the light guides 118 may be vary along the depth of the light guides 118 within the device base 125. In such an example, the thicknesses of the portions of the protection layer 130 extending about the light guides 118 may taper (i.e., narrow or thin) as it extends into the device base 125 from the opening 158 of the light guides 118. The protection layer 130 may be a conformal coating layer. In the illustrated example shown in FIG. 3, the protection layer 130 is of a substantially uniform thickness. In some examples, the thickness of the liner layer 154 may be within the range of about 10 nm to about 1 micron, within the range of about 5 nm to about 100 nm, or within the range of about 50 nm to about 100 nm. In the illustrated example, the liner layer 154 is about 50 nm thick.

The protection layer 130 may comprise any material such that it prevents any solution or liquid, such as the reaction solution, that may penetrate through the reaction structure 126, or the reaction structure 126 and a light guide 118, from interacting with the device circuitry 146, and allows the light emitted from the reaction sites 114 (after treatment with the reaction solution) to pass therethrough and to at least one corresponding light sensor 140 (via at least one corresponding light guide 118). For example, the protection layer 130 may comprise any material that allows light emitted from the reaction sites 114 that is not filtered by the filter material 116 to pass therethrough, and that is chemically inert to the reaction solution. For example, the protection layer 130 may comprise any material that does not chemically react, or chemically reacts to only a relatively small degree, with the reaction solution (which may include a pH equal to or less than about 5 or a pH equal to or greater than about 8, for example) such that the reaction solution does not etch the protection layer 130 or etches less than about one (1) angstrom (Å) of the thickness of the protection layer 130 per hour at about 100 degrees Celsius and at about atmospheric pressure when the reaction solution is in contact with the protection layer 130. For example, the protection layer 130 may comprise at least one oxide, at least one nitride, or a combination thereof. In some examples, the protection layer 130 may comprise silicon dioxide, a metal oxide, a metal nitride or a combination thereof. In some examples, the protection layer 130 may comprise silicon dioxide, silicon oxynitride, silicon monoxide, silicon carbide, silicon oxycarbide, silicon nitrocarbide, silicon dioxide, metal oxide, metal nitride or a combination thereof. In some examples, the pH of the reaction solution is greater than or equal to about 8, and the protection layer 130 comprises silicon dioxide, silicon oxynitride, silicon monoxide, silicon carbide, silicon oxycarbide, silicon nitrocarbide, silicon dioxide, metal oxide, metal nitride or a combination thereof. In some examples, the pH of the reaction solution is less than or equal to about 5, and the protection layer 130 comprises silicon carbide, silicon oxycarbide, silicon nitrocarbide, a metal oxide, a metal nitride or a combination thereof. It is noted that the thickness, formation process and material of the protection layer 130 may be considered and configured (independently or collectively) such that the protection layer 130 prevents any solution or liquid, such as the reaction solution, that may penetrate through the reaction structure 126, or the reaction structure 126 and a light guide 118, from ultimately interacting with the device circuitry 146 (and the liner layer 154 (if provided) and the dielectric material 142).

As discussed above, the light guides 118 may extend from an opening 158 into the device base 125, such as through the dielectric material layers 142 and toward at least one light detection sensor 140. In particular examples, the light guides 118 are elongated and extend from proximate to at least one corresponding reaction recess 108 (from the aperture 158 thereof) toward at least one corresponding light sensor 140 within the sensor base 141. The light guides 118 may extend lengthwise along a central longitudinal axis. The light guides 118 may be configured in a three-dimensional shape that allows and/or promotes the light emitted from the reaction site(s) 114 of at least one corresponding reaction recess 108 to at least one corresponding light sensor 140, such as substantially cylindrical or frustro-conical shape with a circular opening 158. The longitudinal axis of the light guides 118 may extend through a geometric center of the cross-section. However, other geometries may be used in alternative examples. For example, the cross-section of the light guides 118 may be substantially square-shaped or octagonal.

The light guides 118 may comprise a filter material 116 configured to filter the excitation light 101 or a range of wavelengths including that of the excitation light 101, and permit the light emissions from at least one reaction site 114 of at least one corresponding reaction recess 108 (or a range of wavelengths including that of the light emissions) to propagate therethrough and toward at least one corresponding light sensor 140. The light guides 118 may be, for example, an absorption filter (e.g., an organic absorption filter) such that the filter material 116 absorbs a certain wavelength (or range of wavelengths) and allows at least one predetermined wavelength (or range of wavelengths) to pass therethrough. By way of one example only, the excitation light may be about 532 nm and the light emissions from the at least one reaction site 114 may be about 570 nm or more, and therefore the filter material 116 may absorb light of wavelengths of about 532 nm or less than about 570 nm, and allow light of wavelengths of about 570 nm or more to pass therethrough. Each of the light guides 118 of the array may include substantially the same filter material 116, or differing light guides 118 may include differing filter material 116.

Each light guide 118 may thereby be configured relative to surrounding material of the device base 125 (e.g., the dielectric material 142) to form a light-guiding structure. For example, the light guides 118 may have a refractive index of at least about 2. In certain examples, the light guide 118 is configured such that the optical density (OD) or absorbance of the excitation light is at least about 4 OD. More specifically, the filter material 116 of the light guides 118 may be selected and the light guide 118 may be dimensioned to achieve at least about 4 OD. In more particular examples, the light guide 118 may be configured to achieve at least about 5 OD, or at least about 6 OD.

Initially, the reaction sites 114 of one or more reaction recesses 108 of the reaction structure 126 of the device 104 or biosensor 100 may not include a designated reaction, which is generally represented by the lack of shading/patterning in FIG. 4. As discussed above, a reaction site 114 may include biological or chemical substances immobilized to the detector surface 112 or, more specifically, on the base and/or side surfaces of the reaction recesses 108. In particular examples, the reaction sites 114 are located proximate to an opening 158 of at least one corresponding light guide 118 so that pre-designated light emissions emitted from the reaction sites 114 after a designated reaction has occurred via treatment with the reaction solution propagate through the reaction structure 126, through the opening 158 and the filter material 116 of at least one corresponding light guide 118, through the protection liner layer (and potentially the first and second shield layers 154, 155), and to at least one corresponding light sensor 140.

The biological or chemical substances of a single reaction site 114 may be similar or identical (e.g., a colony of analytes (e.g., oligonucleotides) that have a common sequence). However, in other examples, a single reaction site 114 and/or reaction recess may include differing biological or chemical substances. Before a designated reaction, the reaction sites 114 may include at least one analyte (e.g., an analyte-of-interest). For example, the analyte may be an oligonucleotide or a colony thereof (e.g., an oligonucleotide-of-interest). The oligonucleotides may have an effectively common sequence and bind with a predefined or particular fluorescently labeled biomolecule, such as a fluorescently-labeled nucleotide.

Figure 5:
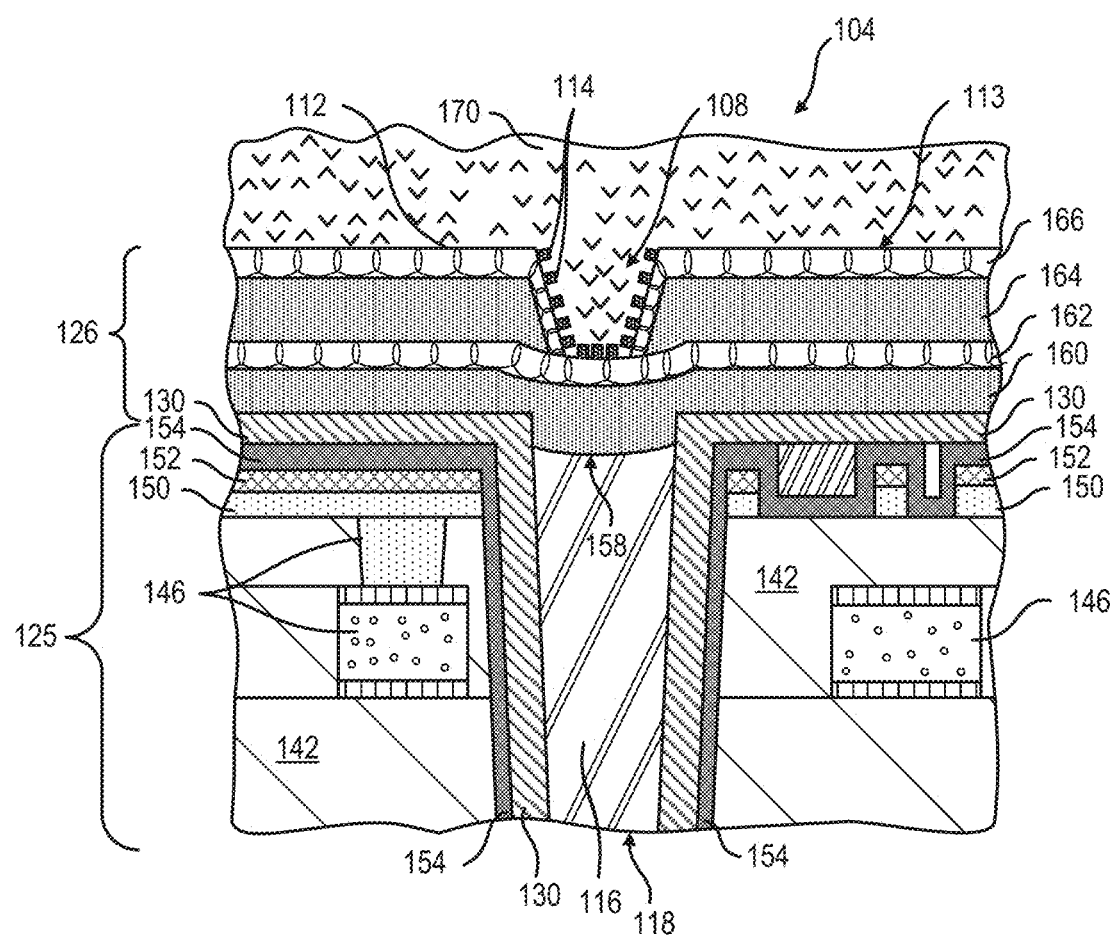
FIG. 5 illustrates, in one example, the enlarged portion of the cross-section of FIG. 4 with reaction solution on the reaction structure.

However, prior to the designated reaction, the fluorophores of the fluorescently labeled biomolecule are not incorporated or bonded to the biological or chemical substances (e.g., an oligonucleotides) at the reaction sites 114, as shown in FIG. 4. To achieve the designated reaction (i.e., to incorporate a fluorescently labeled biomolecule with the biological or chemical substances of the reaction sites 114), the flow cell may provide a flow of the reaction solution 170 to the reaction structure 126, as shown in FIG. 5. The reaction solution may comprise one or more sequencing reagents utilized for DNA grafting, clustering, cleaving, incorporating and/or reading, for example. However, the reaction solution 170 may be any solution. In some examples, the reaction solution 170 may include a liquid. For example, the reaction solution 170 may be an aqueous solution and/or may be comprised of an oil; however, it is understood that the reaction solution 170 may comprise any other liquid. The reaction solution 170 may include one or more constituents that would tend to react with, corrode, dissolve, deteriorate or otherwise render the circuitry 146 inoperable or less effective as circuitry (i.e., transferring signals or electrons). For example, the reaction solution 170 may be an aqueous solution that would tend to oxidize the metal portions of the circuitry 146 if it interacted therewith.

In one example, the reaction solution 170 contains one or more nucleotide types, at least some of which are fluorescently-labeled, and the reaction solution 170 also contains one or more biomolecules, such as polymerase enzymes, which incorporate nucleotides into a growing oligonucleotide at the reaction site 114, thereby labeling the oligonucleotide with a fluorescently-labeled nucleotide. In this implementation, a flow cell may provide a wash solution to remove any free nucleotides that did not incorporate into oligonucleotides. The reaction sites 114 can then be illuminated with an excitation light 101 of at least a first wavelength, causing fluorescence of a second and/or third wavelength in those reaction sites 114 where a fluorescently-labeled nucleotide was incorporated. Reaction sites 114 that did not incorporate a fluorescently-labeled nucleotide do not emit light upon incident excitation light 101.

As shown in the illustrated example in FIG. 5, the reaction solution 170 may be provided within the reaction recesses 108 to achieve the designated reaction of the at least one fluorescently-labeled molecule binding or incorporating with the biological or chemical substances of the reaction sites 114. In some examples, the biological or chemical substances of the reaction sites 114 may be an analyte, and the fluorescently-labeled molecule may include at least one fluorophore that bonds or incorporates with the analyte. In such examples, the analyte may comprise an oligonucleotide, and the at least one fluorescently-labeled molecule comprises a fluorescently-labeled nucleotide.

When the biological or chemical substances (e.g., oligonucleotides) of the reaction sites 114 are similar or identical, such as having a common sequence, the reaction sites 114 may be configured to generate common light emissions after the designated reactions and the excitation light 101 is absorbed by the fluorescently-labeled molecules bonded or incorporated therewith from the reaction solution 170. When the biological or chemical substances (e.g., oligonucleotides) of the reaction sites 114 are not similar or identical, such as having a differing sequence, the reaction sites 114 may be configured to generate differing light emissions after the designated reactions and the excitation light 101 is absorbed by the fluorescently-labeled molecules bonded or incorporated therewith from the reaction solution 170. The filter material 116 of the light guides 118 may be selected or configured to allow any of such light emissions to propagate therethrough and to the light sensors 140, but prevent other such light emissions and/or the excitation light to pass therethrough to the light sensors 140.

Figure 6:
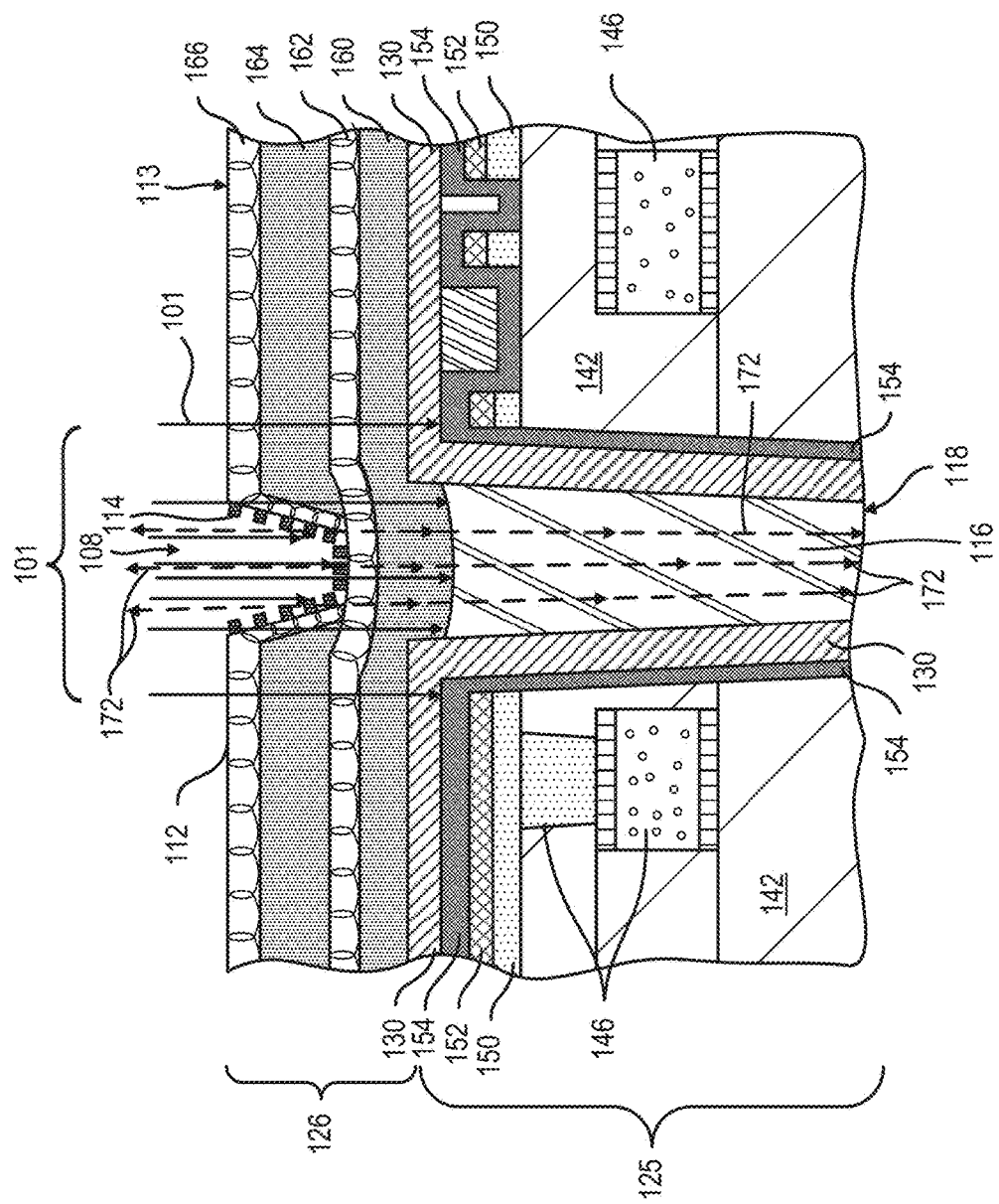
FIG. 6 illustrates, in one example, the enlarged portion of the cross-section of FIG. 4 during a light detection event.

As shown FIG. 6, after the reaction solution 170 has interacted with the biological or chemical substances (e.g., oligonucleotides) of the reaction sites 114, the designated reactions have occurred such that the reaction sites 114 include fluorescently-labeled molecules, such as fluorophores, that emit light of a predefined wavelength or range of wavelengths when excited by the excitation light 101 (i.e., when the excitation light 101 is incident upon the reaction sites 114). The excitation light 101 may thereby be configured based on the fluorescently-labeled molecules of the reaction solution 170 (or vice-versa) and/or a reaction initiated by the reaction solution 170 at the reaction sites 114 and/or a reaction product formed by the reaction solution 170 at the reaction sites 114. As shown in FIG. 6, the reaction sites 114 may emit light signals 172 of a wavelength that differs from excitation light 101 when excited by the excitation light 101 after a designated reaction has occurred via treatment with the reaction solution.

The emitted light 172 from the reaction sites 114 (after treatment with the reaction solution) may travel in all directions (e.g., isotropically) such that, for example, a portion of the light 172 is directed into the at least one corresponding light guide 118, and a portion of the light 172 is directed into the flow channel 119 or the reaction structure 126, as shown in FIG. 6. For the portion that passes into the light guide 118, the device 104 (e.g., the light guides 118 thereof) is configured to facilitate detection of the photons by the at least one corresponding light sensor 140. Specifically, the emitted light 172 from the reaction sites 114 that passes through the opening of a corresponding light guide 118 will be propagated through the filter material 116 thereof to the light sensor 140. The excitation light 101, however, will be absorbed or otherwise prevented from propagating through the light guide 118 to the light sensor 140 by the filter material 116, as shown in FIG. 6. The device circuitry 146 that is electrically coupled to the light sensors 140 transmits data signals based on the photons detected by the light sensors 140. In this way, only the presence of a designated reaction at a reaction site 114 via treatment with the reaction solution will cause emitted light 172 to be detected by the light sensors 140 during a light detection event.

As shown in FIG. 6, a portion of the emitted light 172 from the reaction sites(s) 114 that passes into the at least one corresponding light guide 118 may propagate directly through the filter material 116 thereof and to the at least one corresponding light sensor 140. For example, at least a majority of the emissive light 172 from the reaction sites(s) 114 that passes into the at least one corresponding light guide 118 via the opening 158 may pass directly (e.g., linearly or substantially linearly) through the filter material 116 to the at least one corresponding light sensor 140. A small amount of the emissive light 172 from the reaction sites(s) 114 that passes into the at least one corresponding light guide 118 may travel at an angle such that it passes through the protection layer 130, the liner layer 154 and into the dielectric material layers 142. Such light may be reflected by the circuitry 146 or other metal or reflective structures embedded within the dielectric material layers 142, and potentially back into the corresponding light guide 118 (and potentially to the at least one corresponding light sensor 140). In some examples, the protection layer 130 and/or the liner layer 154 may be transparent to light, such as transparent or substantially transparent at least to the emissive light 172 from the reaction sites(s) 114.

Figure 7:
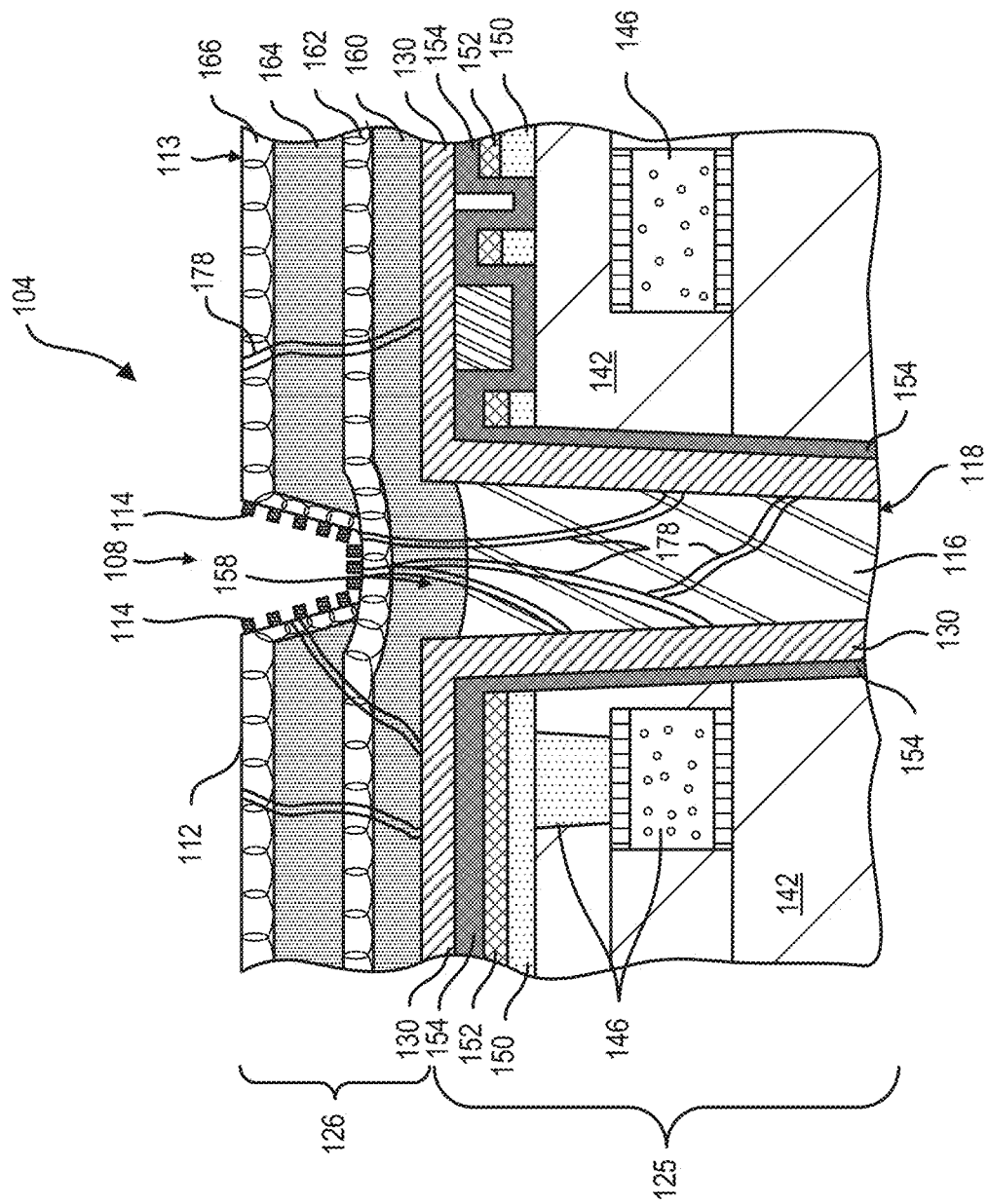
FIG. 7 illustrates, in one example, the enlarged portion of the cross-section of FIG. 4 with discontinuities in the reaction structure and the light guide.
Figure 8:
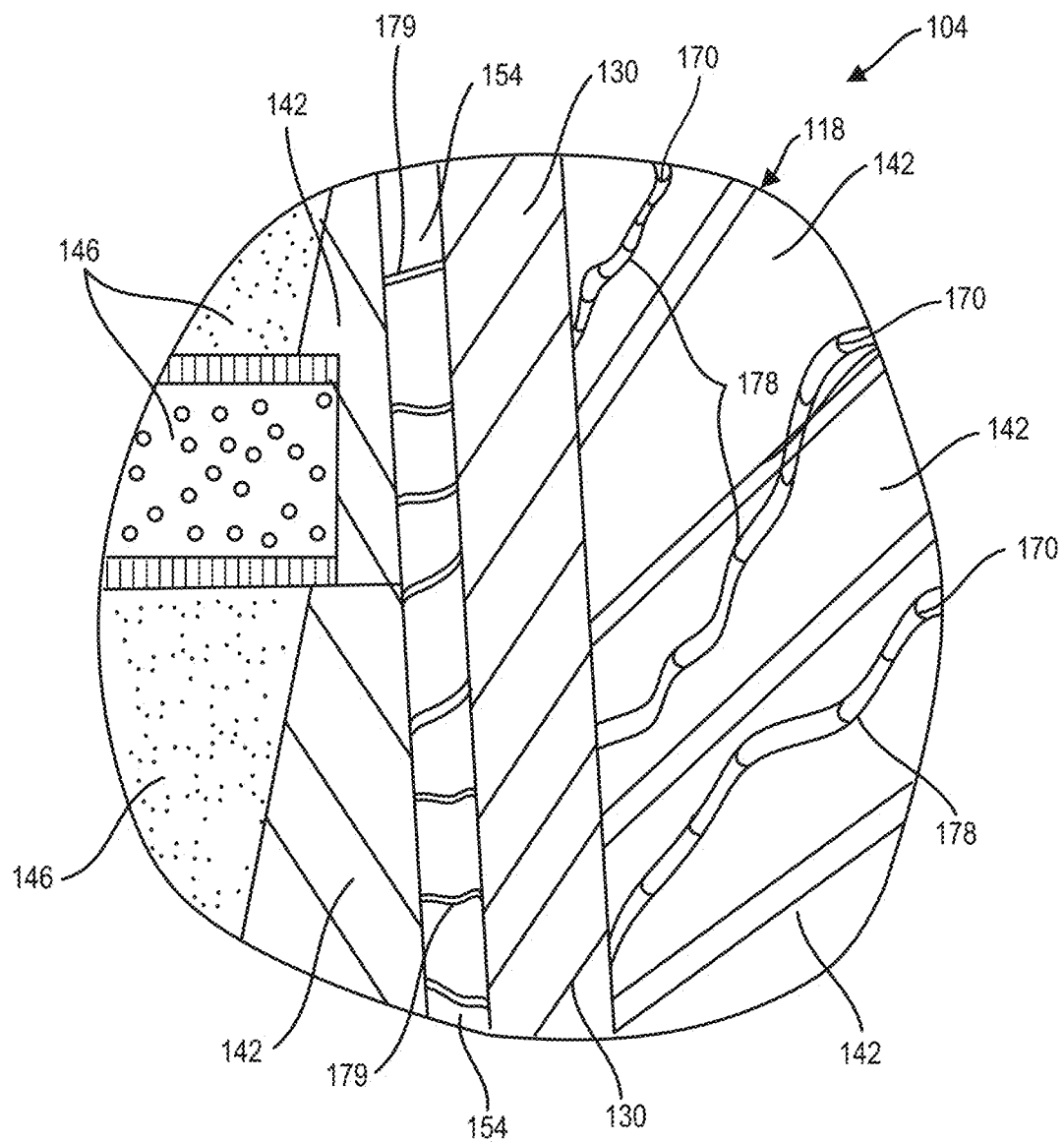
FIG. 8 illustrates, in one example, an enlarged portion of the cross-section of FIG. 7 with discontinuities in the reaction structure, the light guide and a shield layer thereof.

FIGS. 7 and 8 illustrate an example of the device 104 that includes cracks or other discontinuities 178 in the reaction structure 126 and the filter material 116 of a light guide 118. As shown in FIGS. 7 and 8, the reaction structure 126, and potentially the filter material 116 of at least one light guide 118, may include cracks or other discontinuities 178 that extend from the detection surface 112 to the protection layer 130. The discontinuities 178 may extend from the detection surface 112 through the reaction structure 126 to the protection layer 130, and/or extend from the detection surface 112 through the reaction structure 126 and the filter material 116 to the protection layer 130. The discontinuities 178 may thereby allow a solution or liquid to flow from the detection surface 112 into the detection device 104 and interact with the protection layer 130.

It is noted that the discontinuities 178 or other pathways may not be as defined and/or continuous as the depicted discontinuities 178. Rather, the discontinuities 178 represent any pathway that a liquid or solution may take through the reaction structure 126 (i.e., from the detection surface 112) to the protection layer 130. For example, any pathway extending through the reaction structure 126 from the detection surface 112 (e.g., extending through the first layer 160, second layer 162, third layer 164 and fourth layer 166 (if present)) to the protection layer 130 may ultimately allow a liquid or solution (e.g., the reaction solution) to interact with the protection layer 130. As another example, any pathway extending through the reaction structure 126 from the detection surface 112 (e.g., extending through the first layer 160, second layer 162, third layer 164 and fourth layer 166 (if present)) and at least one light guide 118 (e.g., extending through the opening 158 and the filter material 116) to the protection layer 130 may ultimately allow a liquid or solution (e.g., the reaction solution) to interact with the protection layer 130. The discontinuities 178 represent any such pathways.

The discontinuities 178 extending through the reaction structure 126, and/or extending the through the reaction structure 126 and at least one light guide 118, may be formed by any process or mechanism. For example, the discontinuities 178 extending through the reaction structure 126, and/or extending the through the reaction structure 126 and at least one light guide 118, may be formed during the manufacturing stage(s) of the device 104, and/or during use of the device 104, for example. As one specific mode of formation, the discontinuities 178 may be caused by differing thermal expansion coefficients of the materials of the device 104, which may cause the discontinuities 178 to form during the manufacturing stage(s) of the device 104 and/or during use of the device 104. As another example, the discontinuities 178 may be formed by errors in, or naturally occur from, the formation process of the reaction structure 126 and/or the light guides 118. As yet another example, the discontinuities 178 may be formed by the reaction solution or any other liquid or solution) from reacting with and etching through the reaction structure 126 and/or the light guides 118. However, these are just some examples of modes of formation of the discontinuities 178, and the discontinuities 178 may be formed by any mode of operation.

As also shown in FIG. 8 and discussed above, the liner layer 154 may include discontinuities 179 that extend therethrough and would allow a solution or liquid to flow therethrough. The discontinuities 179 of the liner layer 154 may be relatively small internal discontinuities, pores, cracks or the like. The discontinuities 179 of the liner layer 154 may be produced during the manufacturing stage of the liner layer 154 or the device 104, and/or during use of the device 104, for example. The discontinuities 179 of the liner layer 154 may be caused by differing thermal expansion coefficients of material of the liner 154 and other portions of the device 104, for example. As another example, the discontinuities 179 of the liner layer 154 may be caused by formation process thereof. In some examples, the discontinuities 179 of the liner layer 154 may resulting from a liquid or solution interacting with the liner layer 154 and attacking, corroding or otherwise deteriorating the liner layer 154 (and thereby allow the liquid or solution to pass through). However, these are just some examples of causes of the discontinuities 179 of the liner layer 154, any the discontinuities 179 may be formed by any mode of operation. In some examples, the liner layer 154 may be comprised of a material that is chemically reactive with reaction solution such that the reaction solution would etch through the liner layer 154 (and, ultimately, deteriorate the circuitry 146). In some such embodiment, the liner layer 154 may or may not be void of the discontinuities 179.

When the discontinuities 178 are present and the reaction solution 170 (or any other liquid or solution) is introduced onto the reaction structure 126 (e.g., provided over the detection surface 112 and within the reaction recesses 108), the reaction solution 170 (or other liquid or solution) may be able to flow, wick, penetrate or otherwise travel within/through the discontinuities 178 or otherwise through the reaction structure 126, and potentially through the filter material 116 of the light guides 118, as shown in FIG. 8. Further, as also shown in FIG. 8, if the protection layer 130 is not present, the discontinuities 179 of the liner layer 154 would allow such penetrated reaction solution 170 (or other liquid or solution) to continue to travel through the detection device 104 to the dielectric material 142 and, ultimately, interact with the circuitry 146. In another example, the penetrated reaction solution 170 (or other liquid or solution) may chemically react with the liner layer 154 and etch therethrough, and continue to travel through the detection device 104 to the dielectric material 142 and, ultimately, interact with the circuitry 146. As noted above, the reaction solution 170 may be relatively highly acidic (e.g., pH equal to or less than about 5) or relatively highly basic (e.g., pH equal to or greater than about 8), and the liner layer 154 may comprise SiN which is relatively easily etched by such a reaction solution. As also noted above, the reaction solution 170 (or other liquid or solution) may deteriorate or otherwise render the circuitry 146 in operable or less effective the conductive and/or metal portions of the circuitry 146. For example, the reaction solution 170 may chemically react and oxidize the conductive and/or metal portions of the circuitry 146.

However, as shown in FIG. 8, the protection layer 130 may be configured such that it forms a solid continuous barrier layer (without voids, cracks or other discontinuities) that prevents any reaction solution 170 that penetrates through the reaction structure 126, and potentially through the filter material 116 of the light guides 118, via the discontinuities 178 or otherwise from interacting with the circuitry 146 of the device 104. Further the protection layer 130 may be configured such that it is chemically inert with respect to the reaction solution such that the reaction solution (which may include a relatively high acidity or relatively high basicity, as described above) does not etch the protection layer 130, or etches less than about one (1) angstrom (Å) of the thickness of the protection layer 130 per hour at about 100 degrees Celsius and at about atmospheric pressure, when the reaction solution is in contact with the protection layer 130. In this way, although the discontinuities 179 or other pathways through the reaction structure 126 and/or the discontinuities 179 or other pathways through the filter material 116 may be present, the protection layer 130 prevents the reaction solution 170 from flowing to/through the discontinuities 179 of the liner layer 154 and, ultimately, interacting with (and thereby deteriorating) the device circuitry 146. As noted above, the method of formation, thickness and material of the protection layer 130 may be configured, independently or in consideration of each other, so that the protection layer 130 is void of any discontinuities that would allow any solution or liquid (e.g., the reaction solution) from passing therethrough, and the protection layer 130 is chemically inert with respect to the reaction solution such that protection layer 130 is etch resistant (by the reaction solution).

FIGS. 9-13 illustrates an example of a method 200 of manufacturing a light detection device, such as the light detection device 104 of FIGS. 1-8 described. Therefore, like reference numerals preceded with "2," as opposed to "1," are used to indicate like components, aspects, functions, processes or functions, and the description above directed to thereto equally applies, and is not repeated for brevity and clarity purposes. The method 200, for example, may employ structures or aspects of various examples (e.g., systems and/or methods) discussed herein. In various examples, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

Figure 9:
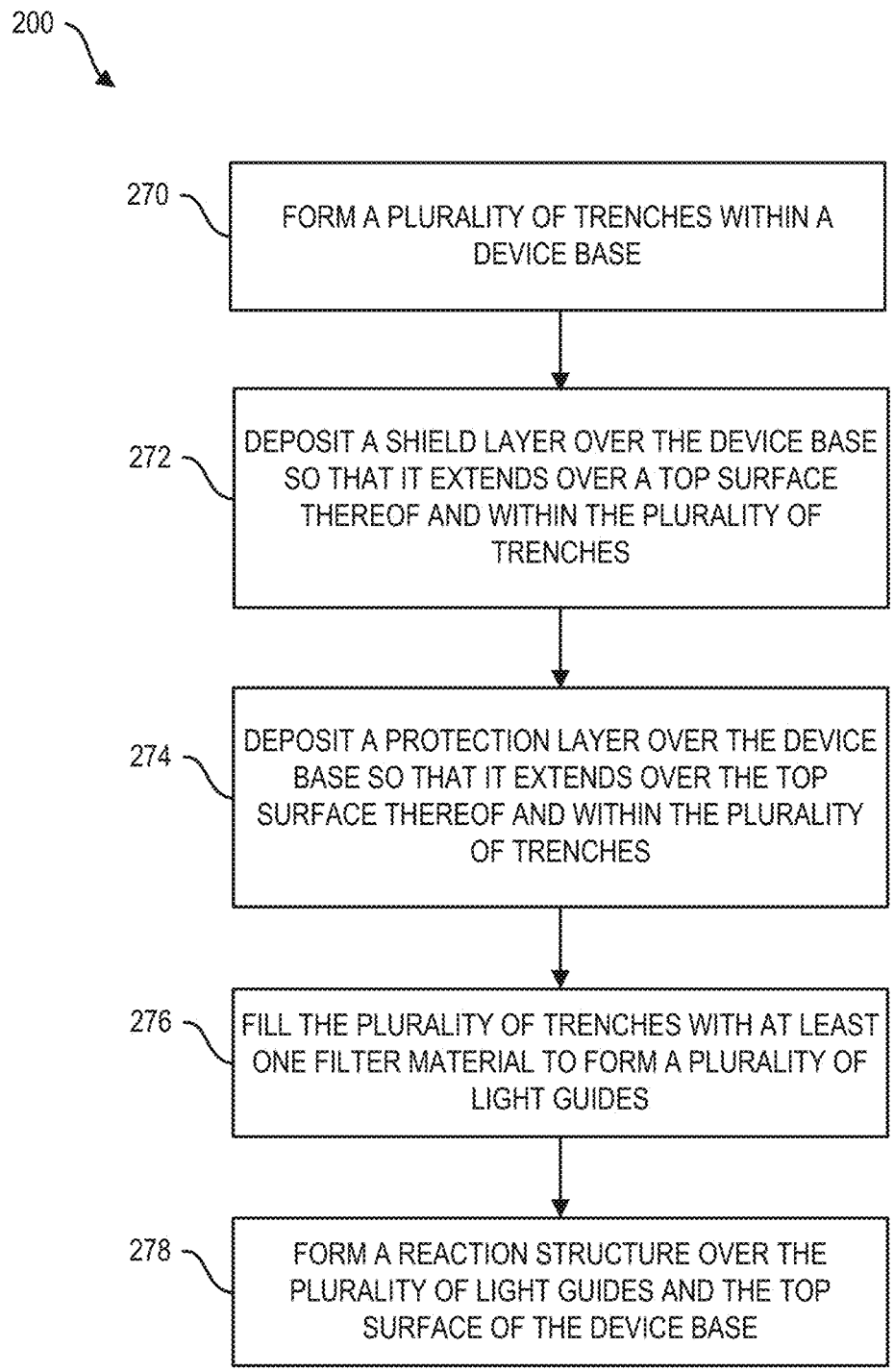
FIG. 9 is a flowchart illustrating, in one example, a method of manufacturing a light detection device in accordance with the present disclosure.
Figure 10:
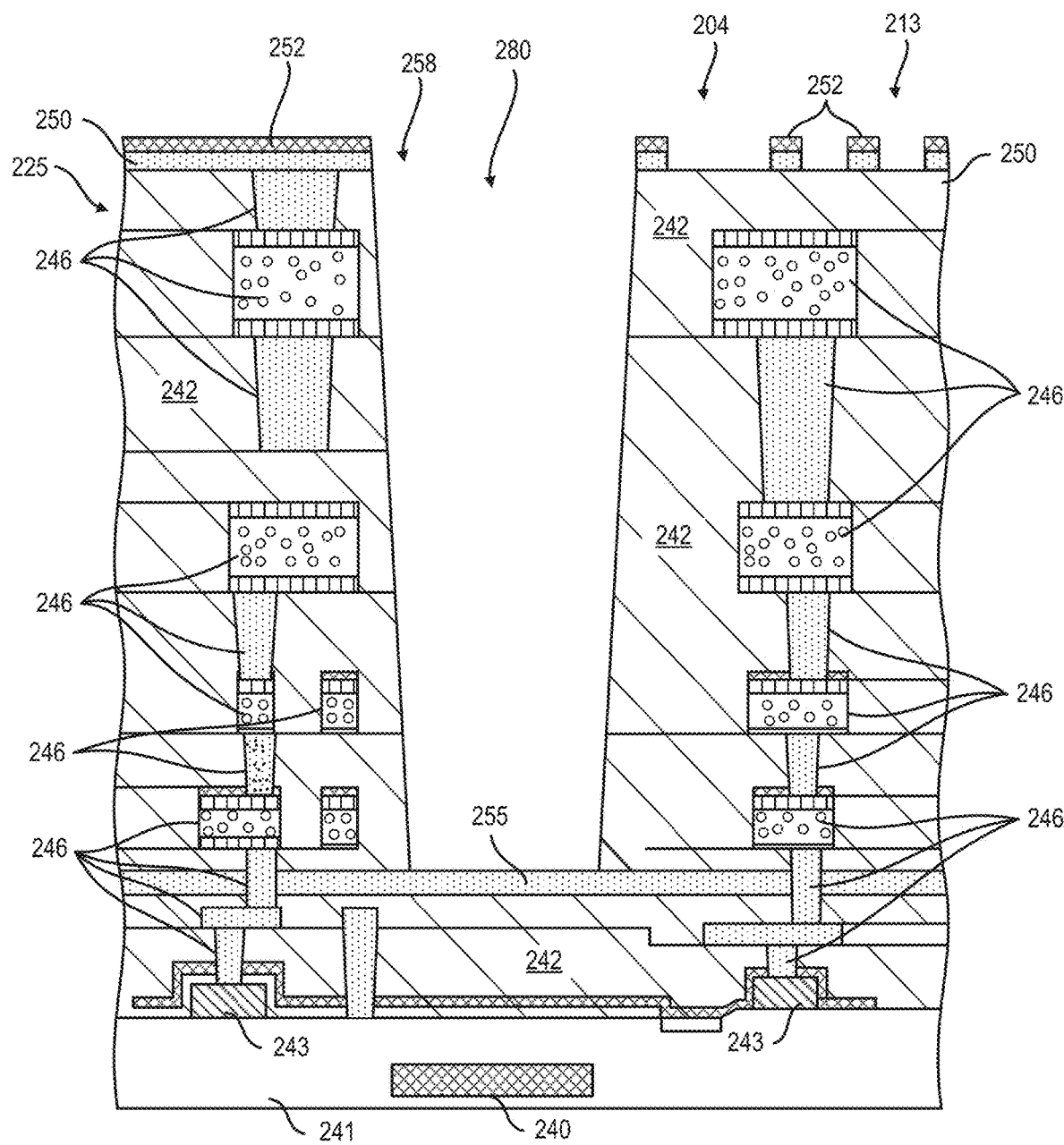
FIG. 10 illustrates, in one example, the formation of a trench in a device base of a light detection device.

As shown in FIGS. 9 and 10, the method 200 of forming a device 204 may include forming (at 270 of FIG. 9) a plurality (e.g., an array) of trenches 280 within a device base 225. The plurality of trenches may extend from an outer/external top surface of the device base 225 and toward at least one corresponding light sensor 240 (through the thickness of the device base 225). As discussed above, the device base 225 may include an array of light sensors 240 and device circuitry 246 electrically coupled to the light sensors 240 that transmit data signals based on photons detected by the light sensors 240. The device base 225 may be provided or obtained via any process. For example, the method 200 may include obtaining the device base 225 in a preassembled or premanufactured state, or include forming or manufacturing the device base 225 prior to forming 270 the plurality of trenches 280.

As discussed above, the device base 225 may be manufactured using integrated circuit manufacturing technologies, such as CMOS manufacturing technologies. For example, the device base 225 may include several substrate layers (e.g., dielectric material layers 242) with different modified features (e.g., metallic elements) embedded therein that form the device circuitry 246. The plurality of trenches 280 may be formed in the substrate layers (e.g., in the dielectric material layers 242) to correspond to portions of the device base 225 that will include, after the method 200, the light guides 218. While only one trench 280 is depicted in FIG. 10, the device base 225 may include an array of light guides 218 as described above, and therefore an array of trenches 280 may be formed.

As shown in FIG. 10, the trenches 280 may extend through openings in the first shield layer 250 and/or second shield layer 252, and through the dielectric material 242 toward at least one corresponding light sensor 240. As shown in FIG. 10, interior surfaces of the device base 225, such as the dielectric material 242 thereof, may define the trenches 280 for the formation of the light guides 218 therein. The trenches 280 may extend to the second liner layer 255 that extends through the dielectric material 242. In this way, the second liner layer 255 may form the bottom of the trenches 280. As also shown in FIG. 10, other openings in the first shield layer 250 and/or second shield layer 252 may be formed in the interstitial areas 213 of the device base 225.

The trenches 280 may be formed by any process(es) or technique(s) that removes the portions of the dielectric material 242 (and potentially portions of the first shield layer 250 and/or second shield layer 252). For example, the trenches 280 may be formed by one or more selective etching processes or reactive ion etching process. In one example, the trenches 280 may be formed by applying at least one mask (not shown) to the device base 225 and removing material (e.g., through etching) of the portions of the dielectric material 242 (and potentially portions of the first shield layer 250 and/or second shield layer 252).

Figure 11:
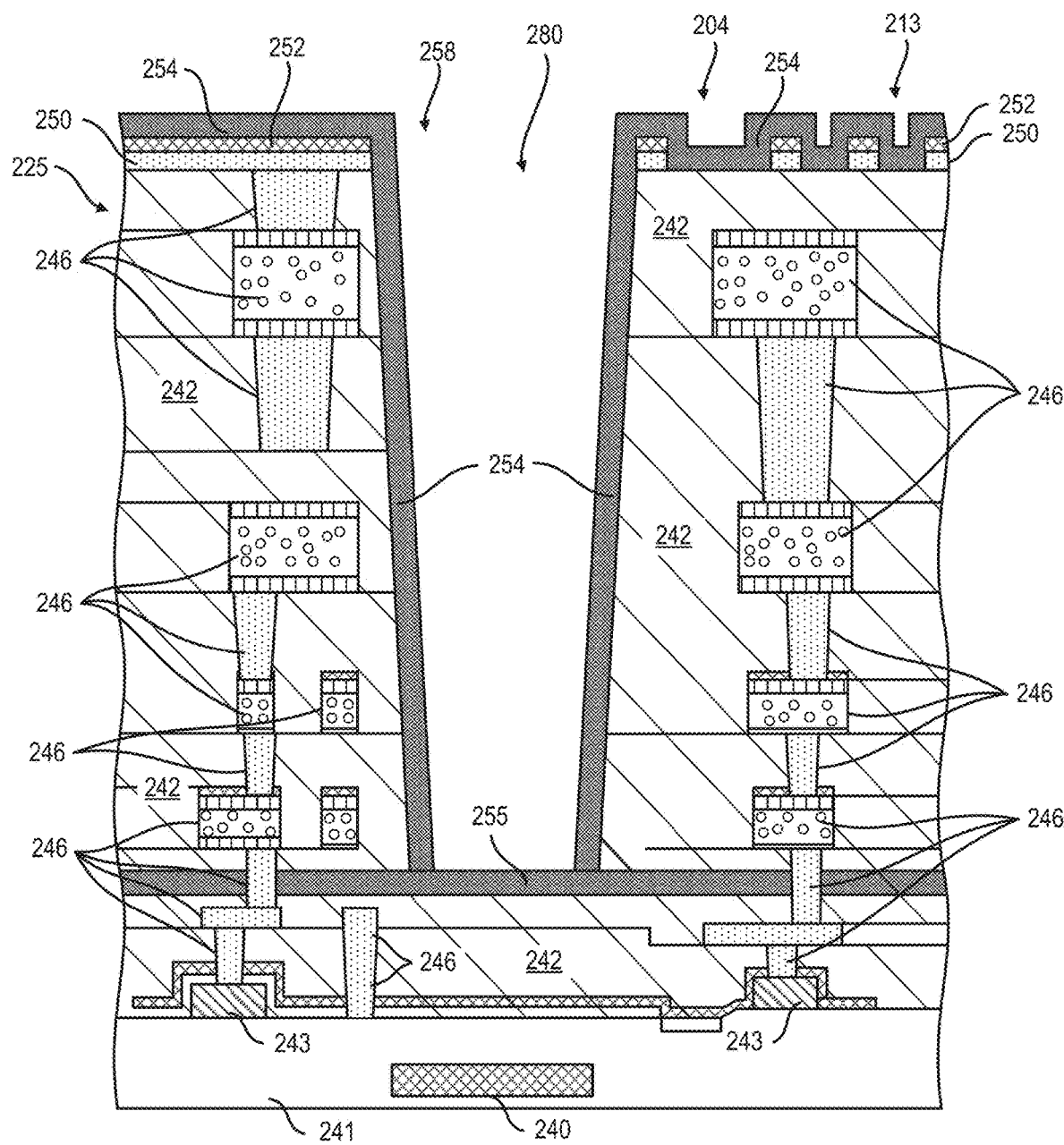
FIG. 11 illustrates, in one example, the formation of a shield layer within the trench in the device base of FIG. 10.

As shown in FIGS. 9 and 11, after formation of the plurality of trenches 280, the method 200 may include depositing (at 272 of FIG. 9) the first liner layer 254 over the top surface of the device base 225 and within the plurality of trenches 280. In some examples, the first liner layer 254 may be formed over the sidewalls of the plurality of trenches 280 and not over the second liner layer 255 at the bottom of the trenches 280. In some other examples, the first liner layer 254 may be formed over the second liner layer 255 at the bottom of the trenches 280, but then subsequently removed. The first liner layer 254 may be deposited over the second shield layer 252 on the top surface of the device base 225, and potentially over any openings in the openings in the first shield layer 250 and/or second shield layer 252 in interstitial areas 213 of the device base 225 such that the second shield layer 252 extends over the dielectric material 242 in such openings, as shown in FIG. 11.

The first liner layer 254 may be formed by any process(es) or technique(s). For example, the first liner layer 254 may be formed by at least one chemical deposition process (e.g., plating, chemical vapor deposition (CVD), plasma enhanced CVD (PECVD), or atomic layer deposition (ALD), for example), a physical deposition process, a growth mode, epitaxy, or a combination thereof. In some examples, the first liner layer 254 may be formed conformally over the surface of the device base 225 and within the trenches 280 (e.g., over the side walls and, potentially, the bottom surface of the trenches 280). The first liner layer 254 may comprise a substantially constant thickness, or the thickness may vary. As discussed above, the first liner layer 254 (and/or potentially the second liner layer 255) may comprise discontinuities (upon formation and/or after use of the device 204) that extend therethrough and allow a solution or liquid to flow therethrough (see FIG. 8). As also described above, the first liner layer 254 may chemically react with the reaction solution (which may be relatively highly acidic or basic/alkaline) such that the reaction solution etches therethrough.

After formation of the first liner layer 254 on the device base 225 (and within the trenches 280), the first liner layer 254 may be further processed. For example, at least the portion of the first liner layer 254 extending over the top surface of the device base 225 (i.e., the interstitial areas 213 of the first liner layer 254) may be processed to flatten/planarize, smooth and/or otherwise improve the surface topography thereof. In some such examples, at least the portion of the first liner layer 254 extending over the top surface of the device base 225 (i.e., the interstitial areas 213 of the first liner layer 254) may be etched and/or polished (e.g., chemical and/or mechanical polishing/planarization) to planarize the outer surface of the first liner layer 254.

Figure 12:
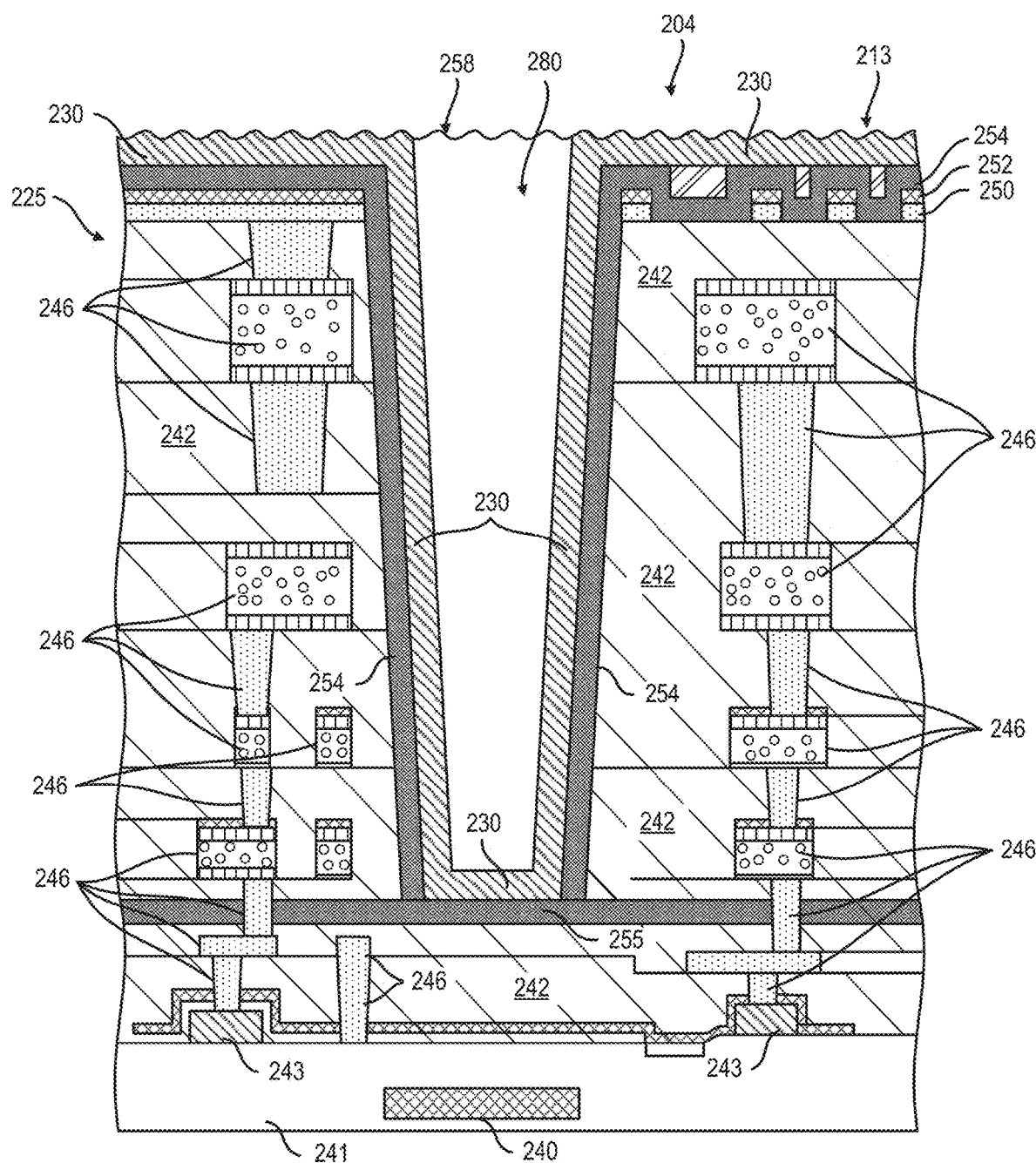
FIG. 12 illustrates, in one example, the formation of a protection layer over the shield layer of FIG. 11.

As shown in FIGS. 9 and 12, the method 200 may include depositing (at 274 of FIG. 9) the protection layer 230 over the device base 225 such that it extends within the plurality of trenches 280. In some example, the method 200 may include depositing (at 274 of FIG. 9) the protection layer 230 over the device base 225 such that it extends within the plurality of trenches 280 and over the top surface of the device base 225. In some examples, the protection layer 230 may be formed over the sidewalls of the plurality of trenches 280 and the bottom of the trenches 280. The protection layer 230 may be formed over the first liner layer 254 and the second liner layer 255.

The protection layer 230 may be formed by any process(es) or technique(s). For example, the protection layer 230 may be formed by at least one chemical deposition process (e.g., plating, chemical vapor deposition (CVD), plasma enhanced CVD (PECVD), or atomic layer deposition (ALD), for example), a physical deposition process, a growth mode, epitaxy, or a combination thereof. In some examples, the protection layer 230 may be formed conformally over the surface of the device base 225 and within the trenches 280 (e.g., over the side walls and, potentially, the bottom surface of the trenches 280). The protection layer 230 may comprise a substantially constant thickness, or the thickness may vary. As discussed above, the protection layer 230 may be formed such that it is void (upon formation and/or after use of the device 204) of any discontinuities that extend therethrough and would allow a solution or liquid to flow therethrough (see FIG. 8). The thickness, material and/or formation process(es) of the protection layer 230 may be configured so that the protection layer 230 is a liquid impervious barrier layer. For example, any process that forms the protection layer 230 as a robust, highly densified layer with a low defect density may be utilized. In some particular examples, the protection layer 230 is formed via an atomic layer deposition (ALD) process or a high-density plasma chemical vapor deposition (CVD) process, for example. The protection layer 230 may thereby be a liquid impervious barrier that prevents and liquid or solution, such as the reaction solution, from interacting with the device circuitry 246 in this device layers of the device base 225.

As also discussed above, the protection layer 230 may be formed such that it is chemically inert with respect to the reaction solution such that the reaction solution (which may include a relatively high acidity or relatively high basicity, as described above) does not etch the protection layer 230, or etches less than about one (1) angstrom (Å) of the thickness of the protection layer 230 per hour at about 100 degrees Celsius and at about atmospheric pressure, when the reaction solution is in contact with the protection layer 230. For example, the composition of the protection layer 230 may not chemically react, or chemically reacts to only a relatively small degree, with the composition of the reaction solution (which may include a relatively high acidity or relatively high basicity) such that the reaction solution does not etch the protection layer 230 or etches less than about one (1) angstrom (Å) of the thickness of the protection layer 230 per hour at about 100 degrees Celsius and at about atmospheric pressure when the reaction solution is in contact with the protection layer 230. The protection layer 230 may thereby comprise an etch resistant layer with respect to the reaction solution (which may include a pH equal to or less than about 5 or a pH equal to or greater than about 8, for example) to prevent the reaction solution from penetrating therethrough (over time) and, ultimately, interacting with and corroding or otherwise interfering with the functioning of the device circuitry 246. The protection layer 230 may thereby be formed to prevent a liquid or solution (such as the reaction solution) that may penetrate through the reaction structure 226 to the protection layer 230, or through the reaction structure 226 and the filter material 216 of a light guide 218 to the protection layer 230, from interacting with the device circuitry 246 (and the liner layer 254 (if provided) and the dielectric material 242).

Figure 13:
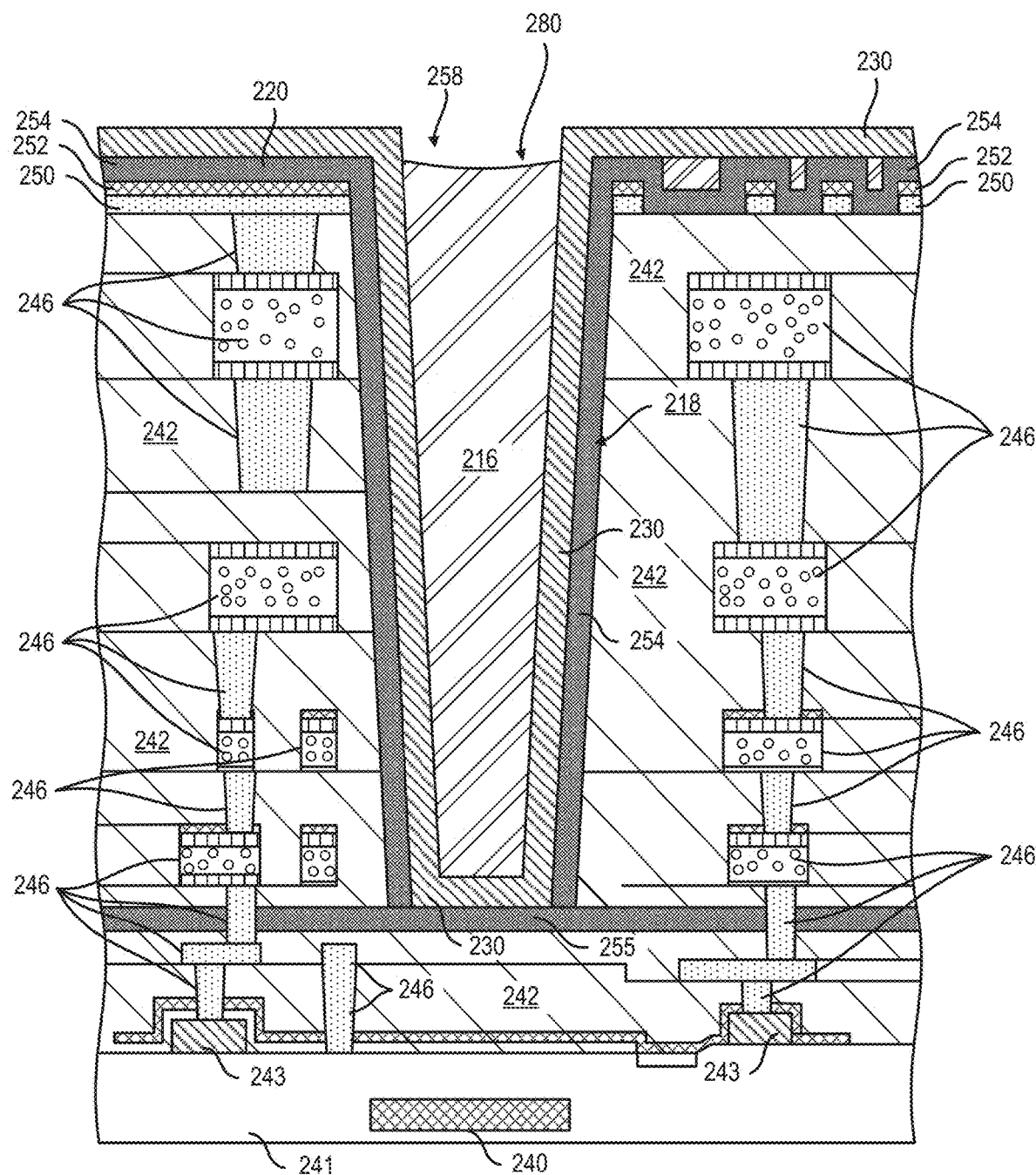
FIG. 13 illustrates, in one example, the formation of a light guide with a first filter material over the protection layer FIG. 12.

As shown in FIGS. 9 and 13, after formation of the protection layer 230, the method 200 may include filling (at 276 of FIG. 9) the plurality of lined trenches 280 with at least one filter material 216 to form the plurality of light guides 218. As discussed above, the at least one filter material 216 may filter light of a first wavelength (e.g., excitation light) and permits light of a second wavelength (e.g., emitted light from reaction sites) to pass therethrough to at least one corresponding light sensor 240. In some examples, the amount of the filter material 216 applied to the device base 225 may exceed the available volume within the lined trenches 280. As such, the filter material 216 may overflow the lined trenches 280 and extend along the top of the device base 225, such as over the first liner layer 254. In alternative examples, the filling operation 276 may include selectively filling each lined trench 280 such that the filter material 216 does not clear/overflow the trench 280 (i.e., extend over the top of the device base 225).

In some examples, filling (at 276 of FIG. 9) the filter material 216 may include pressing (e.g., using a squeegee-like component) the filter material 216 into the lined trenches 280. Optionally, the method 200 may also include removing the filter material 216 from the protection layer 230 and, in some cases, portions of the filter material 216 within the light guides 218. The filter material 216 may be removed from within the light guides 218 so that the opening 258 of the light guides 218 is located at a depth below the protection layer 230, as shown in FIG. 13. Different processes may be implemented for removing one or more portions of the filter material 216. For example, a removal operation may include at least one of etching the portions of the filter material 216 or chemically polishing the portions of the filter material 216.

As also shown in FIGS. 9 and 13, after formation of the protection layer 230 on the device base 225 (and within the trenches 280), the protection layer 230 may be further processed. For example, at least the portion of the protection layer 230 extending over the top surface of the device base 225 (i.e., the interstitial areas 213 of the protection layer 230) may be processed to flatten/planarize, smooth and/or otherwise improve the surface topography thereof. In some such examples, at least the portion of the protection layer 230 extending over the top surface of the device base 225 (i.e., the interstitial areas 213 of the protection layer 230) may be etched and/or polished (e.g., chemical and/or mechanical polishing/planarization) to planarize the outer surface of the protection layer 230.

After formation of the light guides 218 via the filter material 216, the method 200 may include forming (at 278 of FIG. 9) a reaction structure over the plurality of light guides 218 and over the protection layer 230 on the top surface of the device base 225 (see FIGS. 3 and 4). As discussed above, the reaction structure provided over the plurality of light guides 218 and over the protection layer 230 on the top surface of the device base 225 may include a plurality of reaction recesses each corresponding to at least one light guide for containing at least one reaction site and a reaction solution. In some examples, reaction solution with a pH of less than or equal to about 5 or a pH of greater than or equal to about 8 is provided over the reaction structure to form reaction sites thereon. The reaction sites may generate light emissions in response to incident excitation light after treatment with the reaction solution. For example, the reaction solution may initiate a reaction and/or form a reaction product at the reaction sites that generates light emissions in response to the excitation light. As also discussed above, the reaction structure may comprise a plurality of layers. As such, forming (at 278 of FIG. 9) the reaction structure may include forming a plurality of layers over the plurality of light guides 218 and over the protection layer 230 on the top surface of the device base 225 (see FIGS. 3 and 4). The reaction structure may be formed by any process(es) or technique(s).

The protection layer 230 may thereby form an underlying support to the reaction structure. As discussed above, the planarized top surface of the protection layer 230 may thereby minimize surface topography modulation induced in the detector surface of the reaction structure, particularly to the interstitial areas 213 of the detector surface. In particular examples, the processed protection layer 230 may result in a planar and/or smooth surface to the interstitial areas 213 of the detector surface of the reaction structure and prevent the reaction solution or any other biological or chemical substances from remaining thereon and/or prevent pad hopping errors. The flatness of the interstitial areas 213 of the detector surface, provided at least in part by the processed underlying protection layer 230, may enhance the robustness of the detection device 204 as compared to examples that are void of the processed protection layer 230.

Optionally, the method 200 may include providing at least one reaction sites in at least one reaction recess of the formed reaction structure by introducing a reaction solution with a pH of less than or equal to about 5 or a pH greater than or equal to about 8 over the reaction structure and/or mounting a flow cell to the device 204 (see FIG. 1) that provides a reaction solution with a pH of less than or equal to about 5 or a pH greater than or equal to about 8 over the reaction structure. Providing the reaction sites may occur prior to or after the flow cell is coupled to the device 204. The reaction sites may be positioned at a predetermined pattern along the reaction recesses. The reaction sites may correspond (e.g., one site to one light sensor, one site to multiple light sensors, or multiple sites to one light sensor) in a predetermined manner. In other examples, the reaction sites may be randomly formed along the reaction recesses.

As described herein, the reaction sites may include biological or chemical substances immobilized to the detector surface within the reaction recesses. The biological or chemical substances may be configured to emit light signals in response to excitation light. The at least one reaction site may thereby generate light emissions in response to incident excitation light only after treatment with the reaction solution. For example, the reaction solution may initiate a reaction and/or form a reaction product at the at least one reaction site that generates light emissions in response to the excitation light. In particular examples, the reaction sites include clusters or colonies of biomolecules (e.g., oligonucleotides) that are immobilized on the detector surface within the reaction recesses.

It is to be understood that the above description is intended to be illustrative, and not restrictive. For example, the above-described examples (and/or aspects thereof) may be used in combination with each other. In addition, many modifications may be made to adapt a particular situation or material to the teachings of the various examples without departing from their scope. While dimensions and types of materials may be described herein, they are intended to define parameters of some of the various examples, and they are by no means limiting to all examples and are merely exemplary. Many other examples will be apparent to those of skill in the art upon reviewing the above description. The scope of the various examples should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as referee labels, and are not intended to impose numerical, structural or other requirements on their objects. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular example. Thus, for example, those skilled in the art will recognize that the devices, systems and methods described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of examples, it should be readily understood that the disclosure is not limited to such disclosed examples. Rather, this disclosure can be modified to incorporate any number of variations, alterations, substitutions or equivalent arrangements not heretofore described, but which are commensurate with the spirit and scope of the disclosure. Additionally, while various examples have been described, it is to be understood that aspects of the disclosure may include only one example or some of the described examples. Also, while some examples are described as having a certain number of elements, it will be understood that the examples can be practiced with less than or greater than the certain number of elements.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A device, comprising:
   a reaction structure comprising a plurality of reaction sites immobilized thereto; and a
   device base positioned beneath the reaction structure, comprising:
   a sensor base;
   a plurality of light sensors included in the sensor base;
   dielectric material layers stacked on the sensor base;
   a device circuitry electrically coupled to the light sensors to transmit data signals based on photons detected by the light sensors, wherein the device circuitry is provided within the dielectric material layers;
   a plurality of light guides with input regions that receive excitation light and light emissions from at least one corresponding reaction site of the plurality of reaction sites, each light guide extending into the device base toward at least one corresponding light sensor of the light sensors, and said light guides comprising at least one filter material configured to filter the excitation light and to permit the light emissions to pass to the at least one corresponding light sensor;
   a liner layer extending over the device base and about side surfaces of each light guide and positioned between each light guide and the device circuitry; and
   a protection layer extending about each light guide, where the protection layer is chemically inert with respect to a reaction solution that passes over the reaction structure.

2. The device of claim 1, wherein the protection layer abuts the plurality of light guides within the device base.

3. The device of claim 2, further comprising a first shield layer extending between adjacent input regions to block the excitation light and light emissions incident on the first shield layer.

4. The device of claim 1, wherein the protection layer further extends between a top surface of the device base and interstitial areas of the reaction structure extending about the reaction sites.

5. The device of claim 1, wherein the protection layer comprises silicon dioxide, a metal oxide, a metal nitride or a combination thereof.

6. The device of claim 1, wherein the protection layer comprises silicon carbide, silicon oxycarbide, silicon nitrocarbide, a metal oxide, a metal nitride or a combination thereof.

7. The device of claim 1, wherein a pH of the reaction solution is greater than or equal to about 8.

8. The device of claim 7, wherein the protection layer comprises silicon dioxide, silicon oxynitride, silicon monoxide, silicon carbide, silicon oxycarbide, silicon nitrocarbide, metal oxide, metal nitride or a combination thereof.

9. The device of claim 1, wherein a pH of the reaction solution is less than or equal to about 5.

10. The device of claim 9, wherein the protection layer comprises silicon carbide, silicon oxycarbide, silicon nitrocarbide, a metal oxide, a metal nitride or a combination thereof.

11. The device of claim 1, wherein the device circuitry comprises interconnected conductive elements, and the protection layer is configured to prevent the reaction solution from oxidizing the conductive elements.

12. The device of claim 1, wherein a thickness of the protection layer is within the range of about 5 nanometers to about 100 nanometers.

13. The device of claim 1, wherein the reaction structure comprises a plurality of reaction recesses that comprise the reaction sites.

14. A biosensor, comprising:
the device of claim 1; and
a flow cell mounted to the device comprising the reaction solution and at least one flow channel that is in fluid communication with the reaction structure to direct the reaction solution to the reaction sites.

15. A method, comprising:
passing a reaction solution over a reaction structure of a biosensor comprising a plurality of reaction sites, wherein the biosensor comprises:
the reaction structure with the plurality of reaction sites; and
a device base positioned beneath the reaction structure, comprising: a sensor base; a plurality of light sensors included in the sensor base;
dielectric material layers stacked on the sensor base;
a device circuitry electrically coupled to the light sensors to transmit data signals based on photons detected by the light sensors, wherein the device circuitry is provided within the dielectric material layers;
a plurality of light guides with input regions that receive excitation light and light emissions from at least one corresponding reaction site of the plurality of reaction sites, each light guide extending into the device base toward at least one corresponding light sensor of the light sensors, and said light guides comprising at least one filter material that filters the excitation light and permits the light emissions to pass to the at least one corresponding light sensor;
a liner layer extending over the device base and about the side surfaces of each light guide and positioned between each light guide and the device circuitry; and
a protection layer extending about each light guide, where the protection layer is chemically inert with respect to the reaction solution that passes over the reaction structure.

16. The method of claim 15, wherein the protection layer comprises silicon dioxide, silicon oxynitride, silicon monoxide, silicon carbide, silicon oxycarbide, silicon nitrocarbide, metal oxide, metal nitride or a combination thereof.

17. The method of claim 15, wherein the plurality of reaction sites comprise at least one analyte, and wherein the reaction solution comprises at least one fluorescently-labeled molecule.

18. The method of claim 15, wherein the reaction structure comprises a plurality of reaction recesses that comprise the reaction sites.

19. The method of claim 15, wherein the reaction solution has a pH of less than or equal to about 5.

20. The method of claim 15, wherein the reaction solution has a pH greater than or equal to about 8.

* * * * *